(12) United States Patent
Kim et al.

(10) Patent No.: US 6,291,994 B1
(45) Date of Patent: Sep. 18, 2001

(54) ACTIVE Q-DAMPING SUB-SYSTEM USING NUCLEAR QUADRUPOLE RESONANCE AND NUCLEAR MAGNETIC RESONANCE FOR IMPROVED CONTRABAND DETECTION

(75) Inventors: Yong-Wah Kim, Toledo, OH (US); Erik E. Magnuson, Cardiff; David C. Skvoretz, Poway, both of CA (US)

(73) Assignee: Quantum Magnetics, Inc., San Diego, CA (US)

( * ) Notice: Subject to any disclaimer, the term of this patent is extended or adjusted under 35 U.S.C. 154(b) by 0 days.

(21) Appl. No.: 09/483,090

(22) Filed: Jan. 14, 2000

(51) Int. Cl.[7] .................................................. G01V 3/00
(52) U.S. Cl. ......................... 324/300; 324/318; 324/322
(58) Field of Search ................................. 324/318, 322, 324/300, 314

(56) References Cited

U.S. PATENT DOCUMENTS

| | | | |
|---|---|---|---|
| 5,051,700 | 9/1991 | Fox ........................................ | 324/322 |
| 5,500,591 * | 3/1996 | Smith et al. ........................... | 324/307 |
| 5,546,000 | 8/1996 | Maas et al. ............................ | 324/322 |
| 5,592,083 * | 1/1997 | Magnuson et al. ................... | 324/300 |
| 5,594,338 * | 1/1997 | Magnuson et al. ................... | 324/318 |
| 5,804,967 | 9/1998 | Miller et al. .......................... | 324/314 |
| 5,986,455 * | 11/1999 | Magnuson et al. ................... | 324/318 |
| 6,194,898 * | 2/2001 | Magnuson et al. ................... | 324/300 |

OTHER PUBLICATIONS

D.I. Hoult, "Fast recovery, high sensitivity NMR probe and preamplifier for low frequencies"; Rev. Sci. Instrum., vol. 50, No. 2, Feb. 1979.

* cited by examiner

Primary Examiner—Safet Metjahic
Assistant Examiner—Brij B. Shrivastav
(74) Attorney, Agent, or Firm—The Maxham Firm

(57) ABSTRACT

A Q-damping subsystem for either an NQR or NMR contraband detection receiver for effectively reducing the dead time and increasing sensitivity of the contraband detection system. The invention acts as an addition to the standard transmit circuits of NQR and NMR based scanners and spectrometers. The active Q-damping devices require additional circuitry for an NQR/NMR detection receiver and a programming for the control thereof. Typically, the detection receiver generates a high-voltage RF pulse on the order of 200–1000 V with normal operation of 100–300 microseconds in length to provide sufficient magnetic field characteristics to perturb the precessing nuclei. The NQR or NMR detection receiver electronics are very sensitive and have to detect a very weak nuclear induction pulse signal that is in the nano/micro-volt range. The invention encompasses several embodiments of the detection receiver with the Q-damping subsystem which include: a transformer coupled resistive damping circuit; an inductively coupled resistive damping circuit; a shunt capacitor/resistor damping circuit; a grounded shunt capacitor/resistor damping circuit; a common mode choke transient suppression damping circuit; a multi-stage Q-damping circuit; and a full-wave Q-damping circuit.

28 Claims, 19 Drawing Sheets

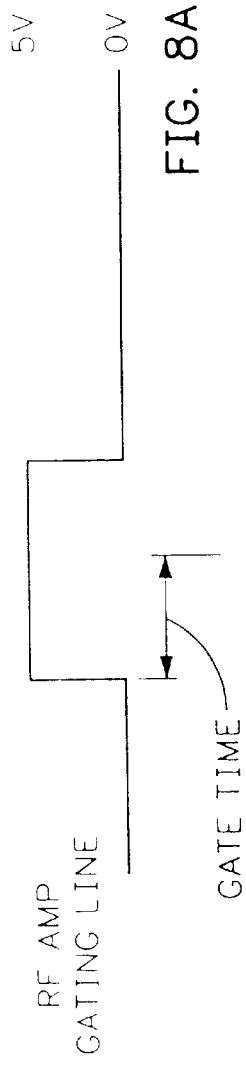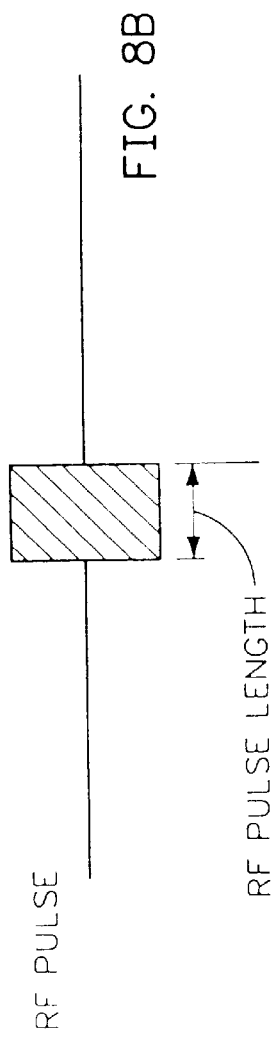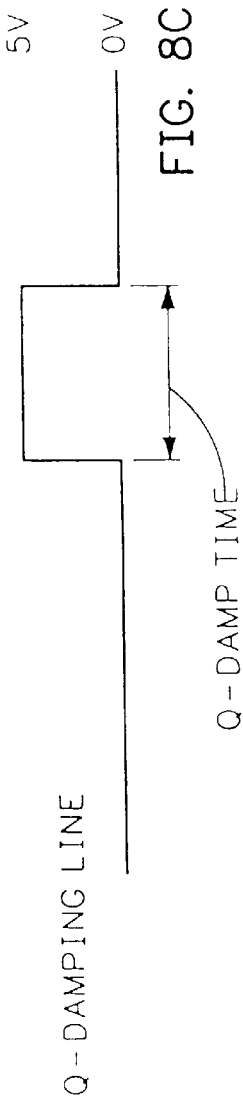

| TIMING | Q1 | Q2 | T.P.1 (C) |
|---|---|---|---|
| EXCITATION | OFF | OFF | + HIGH VOLTAGE |
| Q-DAMP | ON | ON | −5V |
| RECEIVE | OFF | ON | ≈0V |
| NOT USED | ON | OFF | |

FIG. 13D

ACTIVE Q-DAMPING SUB-SYSTEM USING NUCLEAR QUADRUPOLE RESONANCE AND NUCLEAR MAGNETIC RESONANCE FOR IMPROVED CONTRABAND DETECTION

BACKGROUND

1. Field of the Invention

This invention relates generally to a bulk substance detection systems for detecting concealed explosives and narcotics employing either nuclear quadrupole resonance or nuclear magnetic resonance, and more particularly to a practical system and method for Q-damping the detection receiver of a contraband detection system thereby improving operational capabilities.

2. Discussion of the Related Art

Certain atomic nuclei, typically having a spin quantum number of ½, exhibit magnetic signatures when they are within an externally applied magnetic field. This magnetic resonance effect is most commonly observed in $^1$H, and is known as nuclear magnetic resonance (NMR). Atomic nuclei with a spin quantum number of >½ can also show another magnetic signature associated with the interaction of the nuclei with the local electric field. This phenomenon is known as nuclear quadrupole resonance (NQR).

For both of these phenomena, the energy level transitions are observed primarily in the radio frequency range. Detection of these transitions thus requires a radio frequency source to excite the transition, and a radio frequency receiving mechanism to detect the signal. Normally, the signals appear at a pre-defined frequency. An RF coil "tuned" to, or close to, that predefined frequency can excite or detect those signals. The signals are of very low intensity and can only be observed for a short time, approximately 10 μs to 2 ms. As a consequence, there is a need for an NQR or NMR detection receiver that can be tuned to (usually) high Q, has very low noise, and is capable of fast recovery after a high voltage RF pulse. In most conventional resonance (NMR and NQR) experiments, small and fairly homogeneous samples are investigated.

Over the past few years there has been considerable interest in the larger-scale "real world" applications of both NQR and NMR. These applications do not benefit from the luxury of small-scale laboratory investigations. They usually require investigation of large volumes filled with materials of vastly differing physical and chemical composition. Investigation of the contents of mail or baggage for the presence of explosives or narcotics is an example.

With respect to explosives, plastic explosives, have an almost infinite variety of possible shapes and uses for terrorist bombing tactics. Plastic explosives are highly stable, have clay-like malleability and are deadly in relatively small quantities. A small piece of plastic explosive, a detonator, and a trip wire inside a large mailing envelope can cause a deadly explosion. Unfortunately, without close—and potentially dangerous—visual inspection, plastic explosives can be made virtually untraceable. In particular, detection of sheet explosives, typically having a thickness as small as one-quarter inch, has not been effectively accomplished by prior technologies.

The wide-scale attempts to fight the illegal drug trade indicates that narcotics detection is also extremely important. The need for a simple procedure for detecting drugs inside sealed containers, mail parcels, and other small packages, quickly and accurately, is immeasurable. Conventional detection methods are time-consuming, costly, and have marginal reliability.

Detection by means of NQR or NMR is possible for both explosives and narcotics, partially because they have as a constituent element $^{14}$N in crystalline form. Particularly with respect to narcotics, this is true of cocaine base, cocaine hydrochloride and heroine based narcotics. The hydrochloride forms of narcotics, such as cocaine hydrochloride, also contain quadrupolar nuclei $^{35}$Cl and $^{37}$Cl.

A significant factor in contraband detection by means of NQR in particular is that quadrupolar nuclei that are commonly present, and potentially readily observable, in narcotics and explosives include nitrogen ($^{14}$N) and chlorine ($^{35}$Cl and $^{37}$Cl), among possible other nuclei. Thus, in commercial applications, it is necessary to be able to detect quadrupolar nuclei contained within articles of mail, mail bags or airline baggage, including carry-on and checked luggage. While the resonant frequencies of the nitrogen in these substances differs for each chemical structure, these resonant frequencies are well defined and consistent. By applying an RF signal to a container having any of these suspected substances inside, and then detecting any quadrupolar resonance thus engendered by the application of RF pulses, the identity of the contraband substance can be easily determined.

NQR and NMR signals originate from the energy transitions associated with certain nuclei. To minimize noise and radio frequency power requirements and improve detection receiver sensitivity, conventional NQR and NMR systems use a narrow band, high Q, sample coil for both transmitting and receiving. There are, however, a number of factors that can significantly degrade the effectiveness of detecting NQR and NMR signals using this kind of narrow band, high Q, detection apparatus. Some of them are:

(1) the presence of large conductive materials inside the sample coil;

(2) the presence of materials with high dielectric constant inside the sample coil;

(3) temperature variations, which can significantly affect the value of the capacitance used for tuning and matching the RF coil antenna;

(4) mechanical movement of the coil with respect to its surroundings; and (5) changes in size and shape of the coil and/or the shield caused by temperature changes or external baggage loading of the apparatus.

All of these factors can cause serious de-tuning of the detection apparatus, which in turn causes a sensitivity reduction in the detection sensitivity of NQR and NMR signals from the materials inside the sample coil.

Previously, for most applications of NQR and NMR, these conditions have not presented a serious drawback. The apparatus could usually be set up under near-optimum conditions, and the materials being investigated were usually well characterized. However, over the past few years several new applications have arisen which require NQR and NMR apparatus and methods for the detection of certain materials under adverse conditions (for instance, applications in which large volumes of largely unknown materials are under investigation).

Presently used NQR and NMR bulk substance detection systems have fundamental problems with sensitivity and accuracy. These techniques, which are branches of radio frequency spectroscopy, exploit fundamental properties of atomic nuclei. NQR exploits electrical properties of the atomic nuclei, and NMR correspondingly exploits the magnetic properties of the atomic nuclei. Other useful techniques involve nuclear precession, that generates an oscillating nuclear magnetic moment in the atomic nuclei. To observe an NQR or NMR signal from a sample, a radio frequency (RF) pulse is applied to the sample which is in phase with magnetic moments precessional frequency of the sample. This perturbation is momentarily applied to the sample to re-orient the spin of the nuclei in the sample. The nuclei which are not in equilibrium immediately attempt transition to an equilibrium state. As the nuclei return to the equilibrium state, a radio frequency (RF) signal known as the free induction decay (FID) occurs. The inventions RF-coil detects tis signal, which is subsequently amplified and processed. These RF pulses are applied as a pulse train or sequence that in turn generate a series nuclear induction signals that are correspondingly detected, processed and stored.

The sensitivity of an NQR/NMR detection RF coil relies on minimizing the time between the end of the RF pulse and the start of signal detection. The pulse sequence signal is detected between each RF pulse. The pulse spacing time, referred to as $\tau$, depends on the nuclear induction signals characteristic relaxation time and the detection receiver. The nuclear induction signal decays during the pulse train with a characteristic decay time $T_{1p}$, that depends upon the electrical and magnetic environment of the nuclei of interest in $\tau$ time period. The shorter a $\tau$ period is, the longer a $T_{1p}$ ("spin-locking" time constant of the material). To improve the sensitivity of an NQR/NMR detection RF coil, Q-damping of the RF circuit is desirable after a high voltage RF pulse is generated, and subsequently removed as soon as the RF circuit ring down voltage has decayed below a predetermined level.

Prior teachings that deal with "de-Q'ing" of NMR receiver devices include U.S. Pat. No. 5,546,000 entitled "Method for the Reduction of Radiation Damping During Signal Acquisition in NMR Experiments," discloses a method of radiation damping during free induction decay in NMR measurements of samples having a narrow line width uses the active switching of the "Q" factor value of the coil circuit of an NMR detection probe. This teaching is intended for use at high operational frequencies, i.e. in typically very high Larmor frequency (greater than 100 MHz) and radiation damping. Furthermore, this teaching deals a received signals from samples that are so intense that the currents induced in the detection probe act like a low power transmit pulse. This requires a very high Larmor frequency of operation (substantially much greater than the observed NQR frequencies used in the invention herein), a sample volume substantially filled with the nuclide being sampled and a long spin-spin relaxation time $T_2$. In the instant invention, the $T_2$ relaxation time is much less due to the NQR detection system frequency regime of operation and radiation damping is not a problem since the relaxation dead time requires a long $T_2$ time. This teaching does not recognize problems encountered of detecting a short $T_2$ pulse with a long receiver ring-down dead time or problems associated with transients caused by the switching devices after a transmit pulse event for effective contraband detection.

Thus, there is need for hardware that can reduce dead time between the end of the detection head's transmit pulse and the beginning of the data acquisition thereof for efficient and effective specimen analysis while the detection receiver maintains a high-Q characteristic.

SUMMARY OF THE INVENTION

Broadly speaking, this invention provides a practical method and system for improved methods for bulk detection of substances using nuclear magnetic resonance and nuclear quadrupole resonance. The invention is a method of, and subsystem for, selectively Q-damping of an NQR or NMR detection receiver for improved signal-to-noise ratio characteristics and minimizing dead time during data acquisition by the system. This Q-damping system is employed to reduce the RF coil ringdown time, that is, the time it takes for the energy stored in the coil to relax.

The invention herein effectively reduces the dead time between the end of a transmitted pulse and the beginning of the corresponding weak nuclear induction received signal while maintaining high-Q detection receiver characteristics for NQR or NMR applications. This allows a greater proportion of the decaying nuclear induction signal to be detected together with a reduction in pulse sequence separation, that ultimately leads to an increase in sensitivity per unit time. The invention Q-damps the NQR or NMR detection receiver at selected time periods during data acquisition to effectively reduce the T (ring-down time) of the RF coil. The Q of the NQR or NMR detection receiver is reduced only after the application of the high voltage RF-pulse and removed as soon as the ring-down voltage has decayed below a predetermined level. The predetermined level is typically a factor of three (3) less than the minimum detectable signal level. The reason to temporarily apply Q-damping and not reduce "Q" throughout the pulse sequence is because a lower Q-state requires higher transmission power (providing that the pulse width is $>\tau$) and also because detection receiver sensitivity decreases which makes the pickup coil less effective (providing that decay constant for the nuclear induction signal is $>\tau$).

The invention acts as an addition to the standard transmit circuits of NQR and NMR based scanners and spectrometers. The active Q-damping devices require additional circuitry adds to the NQR/NMR detection receiver and a computer program for the control thereof. The transmit circuit generates a high-voltage RF pulse on the order of 200–1000 V with normal operation of 100–300 microseconds in duration to engender sufficient magnetic field characteristics to perturb the precessing nuclei. The NQR or NMR detection receiver electronics are very sensitive and have to detect a very weak nuclear induction pulse signal that is in the nano/micro-volt range. The invention encompasses several embodiments of the detection receiver with the Q-damping subsystem which include: a transformer coupled resistive damping circuit, a direct inductively coupled resistive damping circuit, a shunt capacitor/resistor damping circuit, a grounded shunt capacitor/resistor damping circuit, a common mode choke transient suppression damping circuit, a multi-stage Q-damping circuit and a full-wave Q damping circuit.

BRIEF DESCRIPTION OF THE DRAWING

The objects, advantages and features of this invention will become readily apparent from the following detailed description, when read in conjunction with the accompanying drawing, in which:

FIGS. 8A, 8B and 8C are switching pulse protocols for controlling the Q-damping circuits in FIGS. 6 and 7;

FIGS. 13A, 13B, 13C and 13D show versions of a multi-stage Q-damping circuit for use in the Q-damping circuit of the invention.

DETAILED DESCRIPTION OF THE PREFERRED EMBODIMENTS

Before describing the Q-damping subsystems and detection receivers of the instant invention, FIG. 1 will be described. In particular, commonly used components of the system are described in U.S. Pat. Nos. 5,592,083 and 5,594,338, which are hereby incorporated by reference. The method and system of the present invention can determine the state of the tune of the RF coil in the detector receiver by measuring the amount of power being directly transferred to the RF coil (the "forward" power), and the amount of power being lost due to losses in the circuit and mis-tuning (the "reflected" power) as taught in U.S. Pat. Nos. 5,592,083 and 5,594,338. Once the state of tune of the RF coil has been determined by the values of the forward and reflected power, the coil is retuned by switching inductance or capacitance into or out of the circuit as necessary. The present invention provides Q-damping of the RF coil of the detection head using a Q-damping coil and associated Q-damping circuit.

Figure 1:
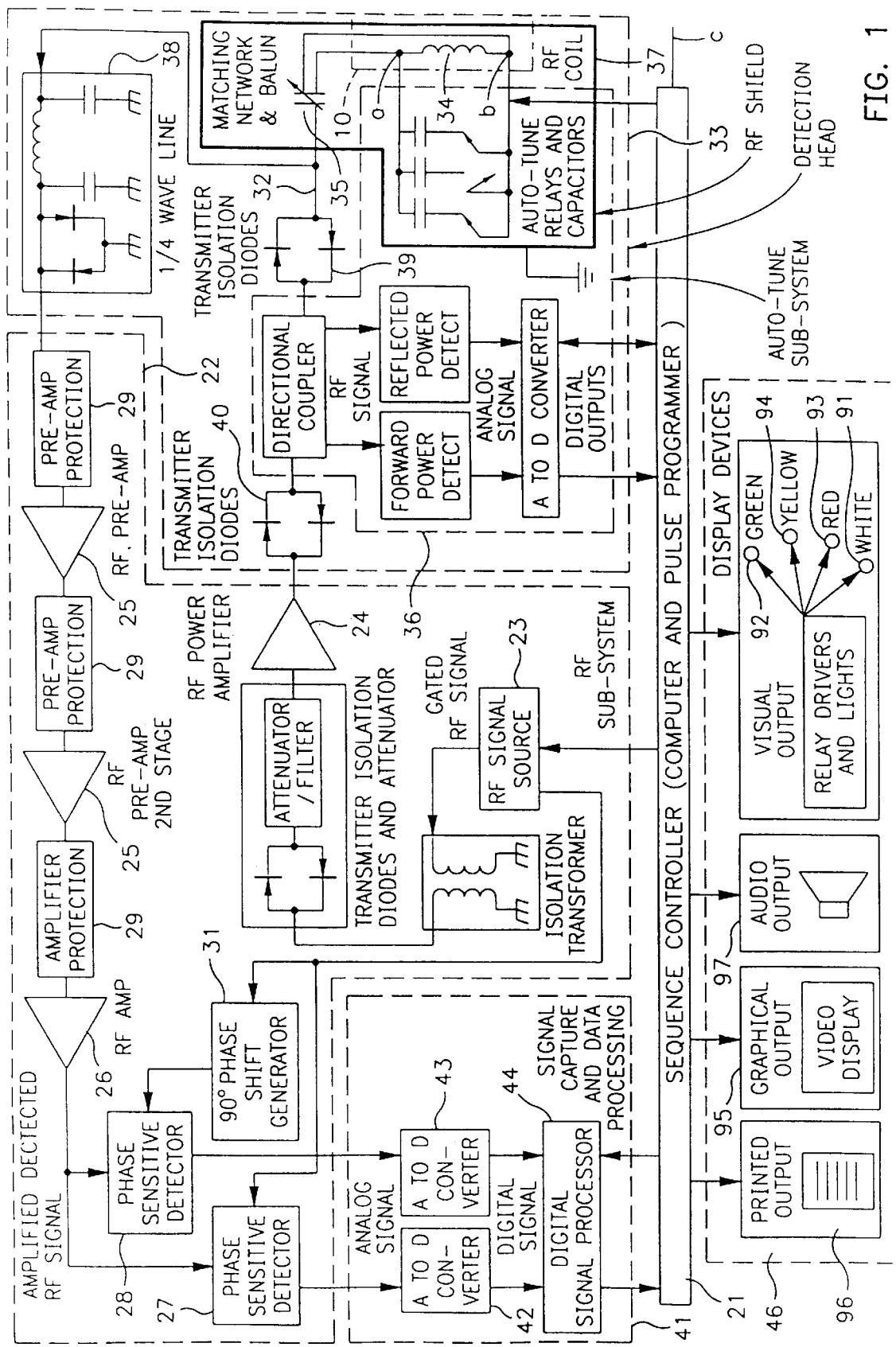
FIG. 1 shows a block diagram of an NQR detection system which includes an automatic tuning apparatus and a Q-damping subsystem of the invention.
Figure 1:
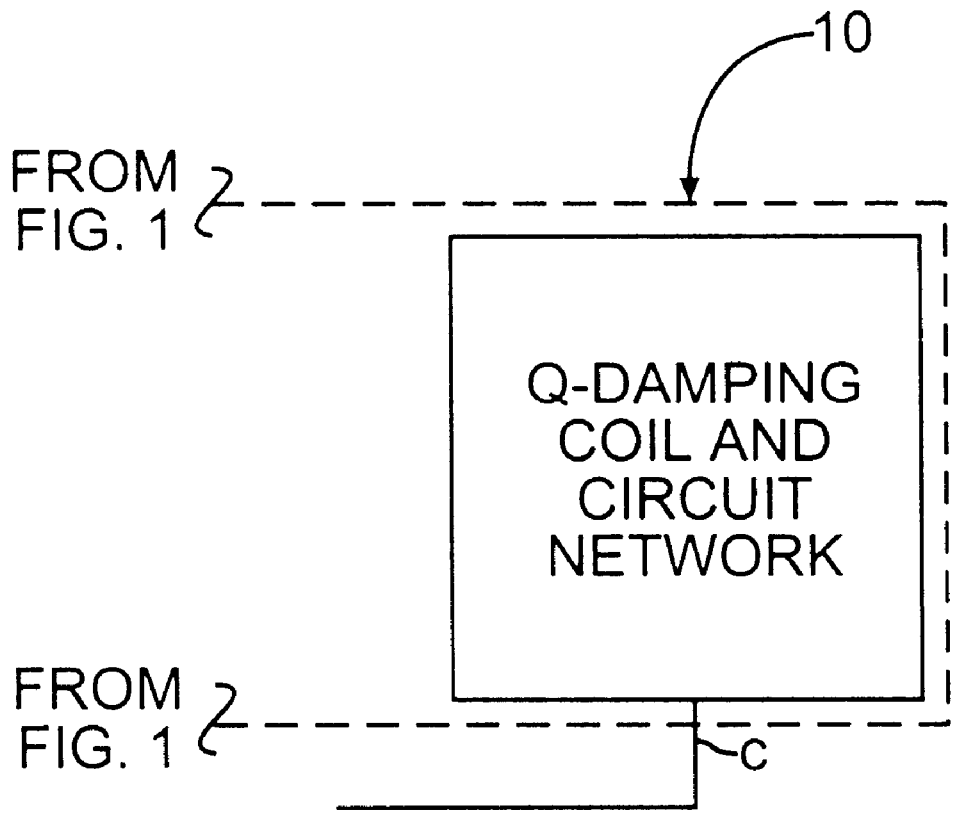

In FIG. 1, the detection system includes an auto-tuning and Q-damping subsystem 10. Terminals a, b, and c are the interference terminals for the Q-damping subsystem 10 that connect to the circuit network embodiments discussed below. A sequence controller 21 is the computer and pulse programmer for the detection system. This subsystem provides precise timing and other control functions for all other elements and subsystems of the invention. It generally would comprise a microprocessor-based device which provides means to download and initialize the sequence control information to all other subsystems, and would include appropriate data storage or memory means. It also stores information on the results of individual scans for future reference. As one specific embodiment, the microprocessor based control and storage device may be a personal computer (PC) with a hard disk or any other appropriate hardware or software, or both.

The sequence controller subsystem also includes a pulse programmer which is a high-precision, high-resolution device that runs off the standard computer bus. The pulse programmer provides the precise sequence control required for correct operation of all other major components in the NQR scanner shown. In combination with the personal computer, it also provides the precisely defined pulses and triggers to activate the subsystems to which it is connected as discussed below.

Radio frequency (RF) subsystem 22 has several functional elements including RF signal source 23, RF power amplifier 24, receiver RF preamplifiers 25, receiver RF amplifier 26 and detectors 27 and 28. The detectors are here shown as phase-sensitive detectors. A 90° phase shift generator 31 is also part of the RF subsystem. This is one embodiment of the invention and is used when detectors 27 and 28 are phase shift detectors. Conventional amplifier protection devices 29 are also part of the RF subsystem.

RF signal source 23 provides either continuous or pulsed RF excitation at a frequency corresponding to the resonant frequency of the sample material. For example, RDX-based plastic explosives have a resonant frequency of approximately 3.410 MHz while PETN-based plastic explosives have a resonant frequency of approximately 890 kHz. The excitation source is fed into amplifier 24 of sufficient power rating to generate about 1 gauss of RF magnetic field within the RF coil. The excitation frequency need not be exactly the same as the target substance NQR frequency but it should be within about 500–1000 Hz. The RF excitation for NQR detection could be a single pulse of 10 $\mu$s–500 $\mu$s duration, depending on the substance being tested for. Such a single pulse could cause an NQR return, but the nuclei may not have reached a steady state of precess so the NQR return might not be sufficiently strong to be detectable or useful. For a letter bomb scanner, approximately three seconds of RF pulses at a repetition rate of 667 pulses per second, meaning a train of 2000 pulses having a pulse width of 200 $\mu$s each, would preferably be applied. The frequency of these pulses can range between 300 Hz and 2 kHz. This would result in a series of NQR signals which are added and averaged in digital signal processor 44. This is an application of the conventional technique where target signals are added linearly while noise adds randomly, thereby building a clearly definable pulse by improving the signal-to-noise ratio (SNR).

The power requirements of the NQR scanner are generally proportional to the detection coil volume. An explosives scanner for mail packages with a 25 liter detector coil volume might have an RF power amplifier rated at about 25 watts, peak value, for example. The amplifier produces a uniform RF field of about 1 gauss over the entire 25-liter volume. In other applications, such as in narcotics detection, the RF field may be greater than this value. For airline baggage, an explosives detection receiver of about 300 liters (10 ft$^3$) requires a 1 to 2 kW RF power amplifier. These parameters are provided for reference purposes and are not meant to define or limit the actual characteristics of a practical NQR system. The Q-damping subsystem power requirements are minimal. For a given cavity geometry, the power is inversely proportional to the RF circuit "Q" as long as the pulse width is greater than 2 Q/T.

The RF excitation pulses are fed from amplifier 24 into detection receiver 33, the operation of which will be discussed below. After the sample in the detection receiver has been excited by the RF pulse, a short RF coil "ring-down" or dead time occurs, during which the receiver is "deaf," before sensing occurs. This ring-down time without Q-damping could, for example, be 500 µs. The Q-damping subsystem 10 reduces the ring down time up to ten times typically and allow more samples to be taken within a given time period, thus improve the SNR. Then RF coil 34 detects the NQR signals and the response is amplified by low-noise, high-gain preamplifier 25 having a gain of 20 to 30 dB, and a noise figure of 1 to 2 dB.

In the package or letter scanner size configuration of the invention, after the received signal has been sufficiently amplified by RF amplifiers 25 and 26, it is fed through a filter into two phase sensitive detectors 27 and 28, having reference signals shifted 90° from each other by means of phase shift element 31. Note that reference RF signal from RF source 23 is applied to phase sensitive detector 27 while the reference signal to phase sensitive detector 28 passes through phase shift element 31. The two mutually phase-shifted analog signals are then fed into signal-capture and data processing subsystem 41, which will be discussed below.

Detection receiver subsystem 33 is comprised of four main components. These are RF coil 34, an RF probe circuit which is RF tuning and matching network 35, RF shield 37, and auto-tune subsystem 36 of this invention. The detection receiver serves two primary purposes. One is to produce a homogenous RF field in the RF coil. The other is to receive the raw NQR signal, if present, from the item under investigation.

RF coil 34, which may also referred to as the receiver or antenna, is made of a highly conductive material, such as copper. The conductor should have a thickness in the order of at least five times the skin depth of the material of the conductor at the operational frequency. This ensures a minimal amount of resistance to the flow of current when the coil is energized with RF. A 25 liter detection volume (for a mail scanning device) has a single turn, high-Q, 0.010 inch-thick copper coil made of a single sheet. The skin depth of copper at 3.4 MHz is about 0.001 inches and the skin depth of copper at 900 kHz is about 0.002 inches.

Direct coil tuning results in an increased overall efficiency for the mail scanning embodiment of the invention. This tuning is accomplished by subsystem 36 of this invention. The single-turn, high-Q coil, when no sample is present, that is, the coil is empty, requires approximately 30,000 pf of capacitance for tuning at about 3.4 MHz in order to detect the $^{14}N$ resonant frequency of RDX explosives. Using a series of switches to add or remove capacitance in order to re-tune the coil under differing load conditions, it has been determined that it would be useful for the system to be re-tunable for a 10% change in tuning capacitance. In this particular application, the coarse tuning increments in capacitance were selected to be approximately 80 pF, and in the fine tuning mode, 10 pf. The RF signal source and amplifier (23, 24) used to exercise the auto-tune subsystem is the same as that used to excite the RF coil for substance detection purposes. Details of the auto-tune subsystem follow.

The automatic fine tuning of the NQR detection receiver under adverse conditions is accomplished in accordance with methodology taught in U.S. Pat. No. 5,594,388. Within sequence controller 21 is software or control programming for the auto-tune subsystem 36 and Q-damping subsystem 10. The auto-tune subsystem is preferably incorporated within RF shield 37, as are RF coil 34, portions of the Q-damping coil and associated circuitry as discussed below and matching network 35. Input/output line 32 connects the tuned RF coil to the amplified RF excitation signal and connects the coil as the receiver of the NQR signals to ¼ wave line 38.

The auto-tune subsystem includes a series of fixed value capacitors switched by an equal number of vacuum relays. The amount of capacitance switched into the tuning circuit is determined by measuring the amount of power being transferred from RF amplifier 24 to RF detector coil 34 (or, more precisely, the amount of "forward" to "reflected" power.) The means to measure this power transfer efficiency consist of a variety of common RF techniques. For one application, a directional watt meter is used to measure the amount of "forward" to "reflected" power. Based on the power transfer efficiency, capacitors are switched in or out of the circuit to maximize power transfer efficiency from the RF amplifier to the RF coil. The system is thus retuned to provide the most efficient and most sensitive RF coil. Once the state of tune of the RF coil has been determined by the values of the forward and reflected power, the coil is re-tuned by switching in capacitance according to the algorithm described below. Tuning of the RF coil consists of two stages: coarse tuning and fine tuning preferably by adjustable capacitance as discussed in the U.S. Pat. 5,594,338.

Physical configurations of the scanner of the system will be described with respect to FIGS. 2, 3 and 4. RF coil 34 is a hollow rectangular tube of thin sheet conductive material, as previously described, formed on thin-walled rectangular insulator 51 (See FIG. 3). Shield 37 is a conductor in the shape of a rectangular copper (or other highly conductive material) sleeve enclosing the coil and spaced from it by a distance of about one half the length of the shortest side of the coil. The shortest side of the coil is represented by distance "X" in FIG. 3 and the spacing is preferably X/2. As an example of actual size, is X is five to six inches, so the spacing between coil 34 and shield 37 would be about 2.5 to 3.0 inches. Another significant measurement is the distance between the edge of coil 34 and opening 52 through which the item to be tested is inserted. That is about the same X/2 distance, or about 2.5–3.0 inches. The RF shield provides the coil and probe units, that is, the structure within the RF shield, with the necessary EMI/RFI (electromagnetic interference/radio frequency interference) shielding from external noise. At the same time, the structure inhibits RFI from escaping from the specimen testing cavity. This configuration has been optimized to provide the best balance between noise isolation of the coil, loading of the coil, and minimization of the total system volume.

Figure 3:
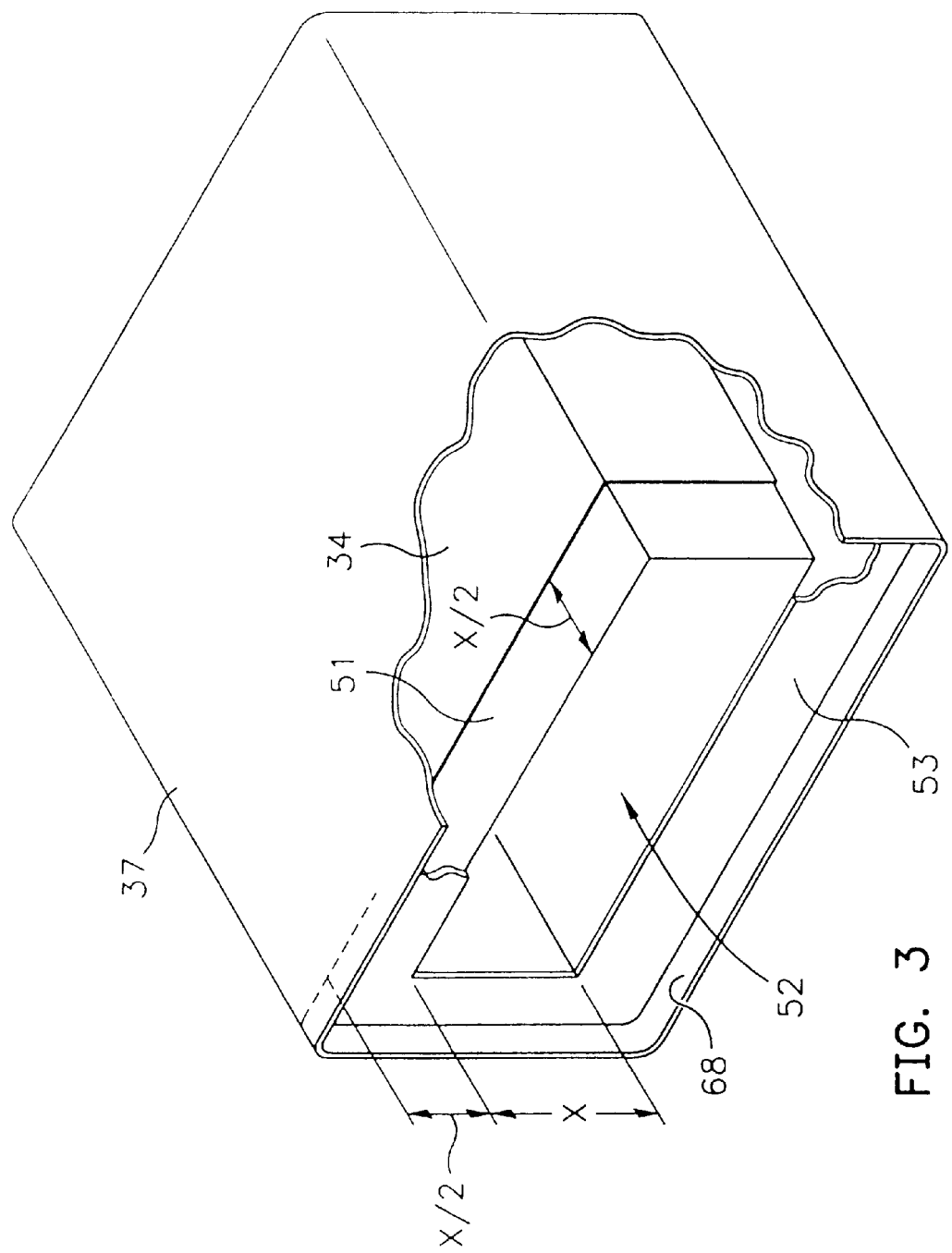
FIG. 3 shows a partially cut away perspective view of the scanner portion of the FIG. 2 device.

To complete the dimensions of the scanner of FIG. 3 for purposes of example, the long (or "y") dimension of the rectangular cavity at the opening may be about 16 inches, and the length of the cavity within the coil may be about 24 inches. Surrounding shield 37 may have a depth of 10–11.5 inches, a width of about 20–22 inches, and a front-to-back length of at least about 27 inches. The volume of the cavity would be about 2000 in$^3$ (26 liters), sufficient to substantially completely surround the specimen (letter, package), that is, it is intended that the specimen be substantially completely with the cavity when being treated. The scanner described above may be referred to as a box with a cavity therein, having external access opening 52 to the cavity.

Different arrangements are necessary for the front and back of the coil. The best RFI shielding is normally an electrically connected and grounded box that completely encloses the RF coil, such that external noise cannot reach the RF coil directly. For most real-world applications of this technology, this arrangement is not always possible. An RFI trap or cut-off device is needed to permit access to one or both ends of the coil for movement of the sample item in and out of the coil. In an application of this invention, the portable hand-fed mail or package scanning device of FIG. 2, only one end is open and this end, door 85, is closed after the package is inserted and before the test is commenced. This closed configuration completes the RFI trap.

Figure 4:
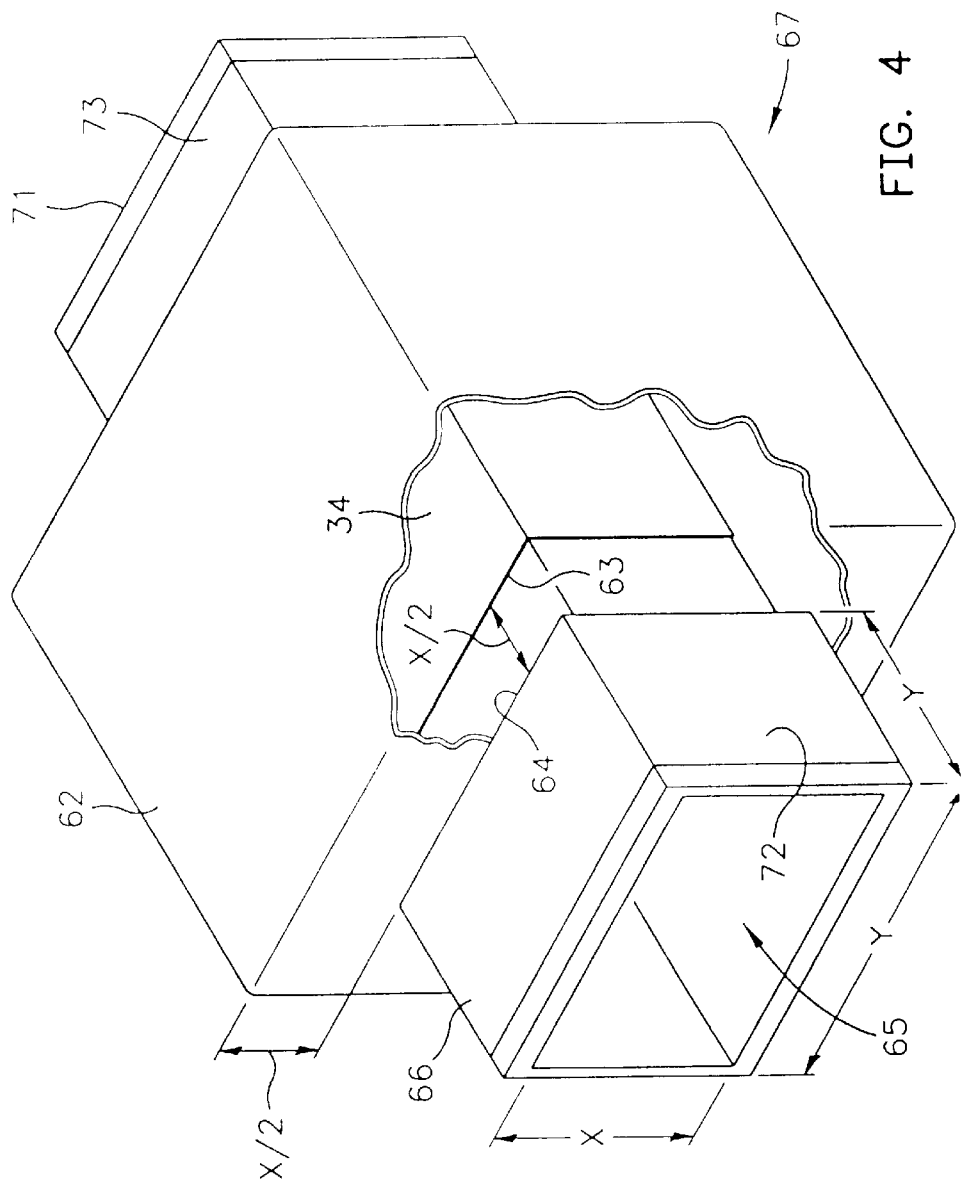
FIG. 4 shows a partially cut away perspective view of a baggage inspection device constructed according to the invention.

For a conveyor system to scan airline baggage, both ends of the RF shield are, of necessity, open, as shown in FIG. 4. To provide the necessary RFI shielding, a tunnel, commonly known as a "wave guide below cut-off" of about the same maximum cross-sectional dimension as the coil, is required. Ends 66 and 71 provide the wave guide below cut-off for this configuration of the invention. While the overall dimensions are greater to accommodate articles of baggage within the coil cavity, the coil, shield and opening relationships remain substantially consistent. In this case the distance between coil 34 and shield 62, X/2, is the same as between edge 63 of the coil and end 64 of the main part of baggage-size scanner structure 67. As an example, the dimension may be 18 inches and the width, dimension "Y," could be around 28 inches. Opening 65 is the same size all the way through wave guide or tunnel end extension 66, the main tunnel (not shown) through test apparatus box 67, and out through wave guide or tunnel end extension 71.

Some additional exemplary dimensions are given here for purposes of completeness. The front-to-back length of the cavity, in scanner box 67, is about 36 inches and the cavity volume would be about 10.5 ft$^3$ (305 liters).

While X/2 is the preferred spacing discussed above, it need not have exactly that relationship to the short dimension of the coil cavity. The shield spacings may range between X/3 and X, with X/2 being preferred at the present time.

In addition to the coil and shield, some typical materials for facing 53 and for the inner rectangular frame are wood and plastic. They should be relatively light, rigid, and be an electrical insulator. In the larger, double open-ended version of FIG. 4, external surfaces 72 and 73 of tunnel ends 66 and 71 would likely be copper or aluminum, while the inside and facing would be plastic or wood.

Figure 2:
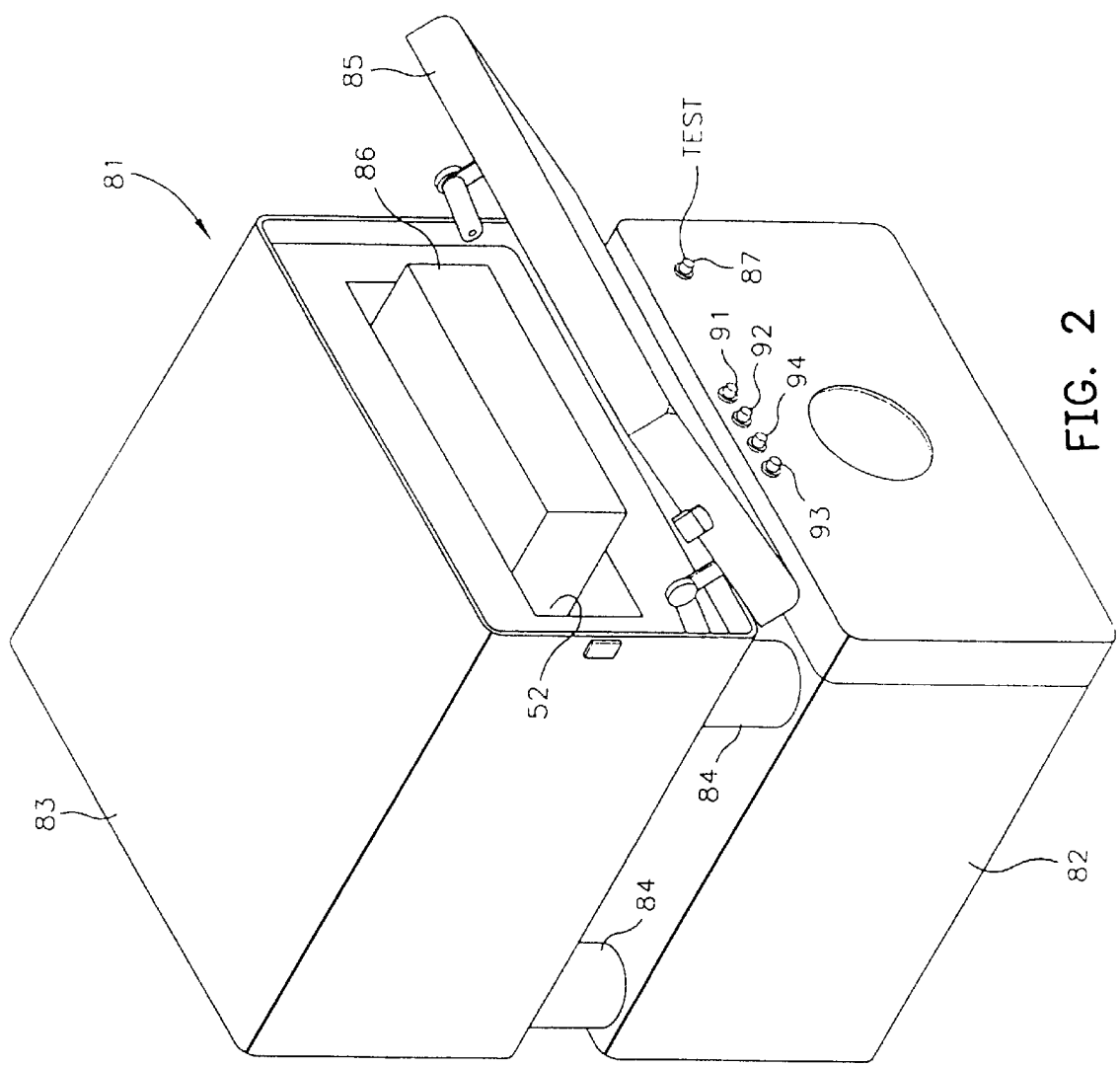
FIG. 2 shows a perspective view of an actual device in accordance with the invention for small package inspection incorporating the system of FIG. 1 therein.

A practical smaller size, or portable, mail scanner 81 is shown in FIG. 2. The electronics and control functional elements can be contained in box 82. The scanning device itself is box 83 mounted on top of box 82 by stand-offs 84. The front of scanner 83 is normally closed by front door or lid 85 which is hinged to the top box. A package 86 is shown in opening 52, within the RF coil, ready for testing after it is fully inserted and door 85 is closed.

The portable mail scanner of FIGS. 2 and 3 has only one end of the coil that is required to be open for access to the coil compartment or cavity. The shield entirely surrounds the coil, except for an opening of the same cross-sectional area as the coil. This opening forms a slot through which packages can be passed. The opening in the shield is positioned in such a way (approximately two to three inches from the end of the coil) that the magnetic flux from the coil is "forced" to be contained within the shield itself. Thus, little flux escapes from the shielded opening and little flux can enter the cavity. In order to further minimize EMI/RFI noise entry, a secondary shield in the form of a grounded, aluminum enclosure, with EMI/RFI gaskets and a lid which overlaps the coaming, is employed. This is preferably an aluminum casing closely surrounding shielding 37 and does not add to the overall dimensions, except to make overhang 68 if desired. This overhang is both aesthetically pleasing and provides improved RFI shielding for external RF. Lid 85 covers opening 52 with package 86 in the cavity. Suitable rubber gaskets impregnated with conductive material completes the EMI/RFI shielding.

Once the auto-tuning procedure has been completed, the scanning procedure begins. The scanning procedure is standard for detecting NQR signals in real-world detection applications. In one application of this invention, the procedure consists of a combination of RF pulses, commonly known as PAPS (phase-alternated pulse sequence) and NPAPS (non-phase-alternated pulse sequence) versions of the SSFP (steady state free precession) pulse sequence. These sequences are described in U.S. Pat. No. 5,365,171, which is incorporated herein by reference to the extent necessary for full explanation. However, there are other sequences of RF pulses which are commonly used in NQR procedures which are also applicable for use in this invention. These are known and readily useable by those of ordinary skill in this technical field.

When test button 87 is pushed (FIG. 2), the coil is tuned and scanning of the package is accomplished and at least one of the lights is illuminated. White light 91 flashes while tuning and testing are being completed. Illumination of green light 92 indicates that no contraband being tested for is present. Illumination of red light 93 indicates that the target substance has been found in such a quantity as to be significant. If yellow light 94 is illuminated, it means there may be something present which should be looked at or further tested. It could mean there is a significant amount of metal present. Both yellow and green lights illuminated means there was no clear NQR signal and there was metal or other conductive material present. Both red and yellow lights illuminated indicates that the target substance may be present, but it is at least partially obscured by metal. Those are indeterminate results. Not shown is an ON/OFF button on a non-visible side of unit 81.

One challenge which must be overcome in proceeding from the laboratory to a practical NQR detection system for scanning airline baggage is that of acoustic ringing. A standing wave can be set up in a conductor placed in a pulsed RF field. This acoustical wave is picked up by the RF coil. The signal produced is often close to the same magnitude and sufficiently close in characteristics to an NQR signal to possibly cause a false alarm. The acoustical signal is often coherent with the exciting RF pulse, and hence can potentially be mistaken for an NQR signal, which is also coherent with the exciting RF pulse. Moreover, common methods for reducing spurious ringing effects in laboratory NQR systems, such as signal averaging and/or reversing the RF phase, will often not sufficiently reduce the problem in practical systems in the field. Certain types of commonly-occurring materials, such as spring steel, are particularly prone to acoustic ringing.

A simple but effective method of reducing the effects of acoustic ringing in NQR detection applications is employed. The primary differing characteristic of an NQR signal compared with an acoustic ringing signal is that NQR signals occur only at pre-defined frequencies. Acoustic ringing signals, on the other hand, can be generated by any frequency of an RF excitation pulse. Thus, by operating the NQR scanning system at a frequency outside the range of the NQR sample frequency, using a standard or modified RF pulse sequence, no signal will be generated by or be detected from any target material. Under these conditions, if a signal is seen, it is from acoustic ringing. Implementation of this method is straightforward. The "ring detect" sequence can be implemented before or after the main sample detect sequence and is part of the programming and RF signal generation. This frequency excursion can easily be provided by the auto-tune aspect of this invention.

As an alternative for detection of acoustic ringing, the standard target substance detection scanning cycle can be employed. It is a principal of acoustic ringing that the ringing signal decays with time. Within a limited time period, between respective RF pulses, the NQR signal increases with time. This feature can be used to determine the nature of the signal response. This procedure can be used in some instances, and is limited at the highest sensitivity levels, where the noise level of the system is comparable to the signal level. Additionally, the Q-damping subsystem 10, described fully hereinbelow, improves the SNR.

In the package or mail scanner configuration of this invention, when employing analog detectors, signal capture and data processing subsystem 41 comprises two analog to digital (A/D) converters 42 and 43 and digital signal processor 44. The received signals from phase sensitive detectors 27 and 28 are fed to A/D converters 42 and 43 respectively. All signals produced by the sample scan and ring detect sequences are fed into the A/D converters and are processed by the digital signal processor. Through the sample scan sequence, signals are either added or subtracted, according to the algorithm outlined in U.S. Pat. No. 5,365, 171. The addition/subtraction algorithm reduces RF coil ring-down effects and magnetoacoustic ringing.

In a practical configuration of this portion of the invention, signal capture and most of the signal processing is carried out on a plug-in PC A/D converter card. The card has two channels, 14-bit resolution, and a 2 MHz sampling rate. Subsystem 41 also performs on-board digital signal processing functions, such as addition or substraction of consecutive data sets as required. Once processing the output signal is completed, it is digitally filtered and compared to a predefined threshold level. Alternatively, once the signal is apodized and Fourier-transformed, it occurs as a quadrature "spike" at or close to zero Hz in the frequency spectrum, and is then filtered and compared to the "known" signal of the material sought to be determined.

In the frequency domain, the signal capture and data processing subsystem compares other signal factors to the expected signal factors. For example, it may compare the signal shape (Lorentzian or Gaussian) to the line-width at half height. A combination of the above signal factors may be used to determine the presence or absence of the target substance. The output of the digital signal processor is then sent to display device 46.

The NQR detected signal is compared with a predetermined threshold level stored in the memory of digital signal processor 44. If the detected signal is equal to or greater than the predetermined threshold, red light 93 flashes on the operator's panel on display device 46, indicating the presence of the target substance. If the signal is less than the predetermined threshold, green light 92 flashes, indicating the absence of the target substance. If the auto-tune algorithm detects that an excessive amount of re-tuning of the coil is necessary, compared to an average investigation or predefined threshold, or an acoustic ringing signal is detected, the condition is flagged and yellow warning light 94 illuminates. The yellow warning light indicates that: (1) there is an abnormally high amount of metal in the coil, (2) a high-quantity of high dielectric material is detected, or (3) a spurious acoustic signal has been detected. Further alternative testing or visual inspection can be used to resolve inconclusive results of the NQR test.

In addition to the illumination indications mentioned above, the display device can optionally provide graphical display 95 of the signal showing both the in-phase and quadrature signals, as well as other signal and system characteristics. Also optionally, printed output 96, including the time, date, signal amplitude and frequency, as well as coil tuning parameters can be provided, other information, such as acoustic signal responses from speaker 97, could be made available if desired.

The factors which have degraded the effectiveness of previous NQR signal detectors are reduced or eliminated by this system. If conductive or high dielectric materials are present in the sample, the auto-tune sub-system will be employed in an attempt to neutralize the effect of the foreign material. Then visual inspection can be accomplished if there is reason to do so. The auto-tune capability can quickly account for changes in temperature which affects tuning capacitance, as well as movement or distortion of the coil which might occur when samples are put into the cavity.

To further describe the detection system of FIG. 1, RF probe 35 is a matching network and Balun which provides tuning and matching of the coil, and also protects preamplifiers 25 from the high voltages in the coil during RF excitation. RF probe 35 matches RF coil 34 to a 50Ω unbalanced input. This makes the coil look like a 50Ω transmitter/receiver and is conventional matching technology. The function of ¼ wave line 38 is to isolate the receiver from the transmitter. Transmitter isolation diodes 39 and 40 have a related function. The auto-tune subsystem determines the state of the tune of RF coil 34 in the detector receiver by matching the RF coil to its load in the detection volume. It measures the amount of power transferred directly to the RF coil (the "forward" power), and the amount of power reflected back due to losses in the circuit and mis-tuning (the "reflected" power). Once the tuning state is determined comparing the values of the forward and reflected powers, the coil is re-tuned by switching capacitance according to a predetermined sequencing.

When coil 34 is loaded with a package of unknown contents, it becomes de-tuned. To re-tune the RF coil, vacuum relays can switch an array of capacitors arranged in pF values of powers of two, for example, 10, 20, 40 and 80. This particular arrangement is capable of producing up to 256 values of capacitance for re-tuning the system if eight switching elements are used, with a maximum total of 3000 pF. Rather than overloading the system with one relay for each value of capacitance, this power arrangement minimizes the number of relays needed to produce a given value of capacitance (e.g. 10+20=30; 20+80=100, etc.), and affords very fast operational speed. It should be noted that the same algorithm can be used with a continuously-variable capacitance system. A stepper motor could be used and the actual tuning sequence would be very similar to that described for discrete, direct capacitor tuning. Using capacitors switched by vacuum relays requires a "settling time" of about 6 ms or less to allow the relays to operate and for the reflected power to achieve a steady-state value. The benefit in overall system ruggedness, efficiency, reliability, and small size due to the fixed switch capacitor scheme overcome any possible advantage in precision tuning which might have been achieved using the more conventional variable capacitors. However, because the system uses switching commands controlled by a computer operated sequence controlling device, it can get exact information on the amount of system de-tuning. The auto-tuning subsystem of the detection system offers improved sensitivity for NQR systems. Additionally, adjustable inductance tuning can provide fine tuning for the system if incorporated.

The factors which have degraded the effectiveness of previous NQR signal detectors are reduced or eliminated by this system. If conductive or high dielectric materials are present in the sample, the auto-tune sub-system attempts to neutralize the effect of the foreign material. Then visual inspection can be accomplished if there is reason to do so. The auto-tune capability can quickly account for changes in temperature which affects tuning capacitance, as well as movement or distortion of the coil which might occur when samples are put into the cavity. The tuning system is a specific component of an NQR scanner system. Because NMR detector systems also require variable RF frequencies to be applied and detected, this has direct application to those detector systems as well. The auto-tuning function is equally applicable to NQR and NMR detection systems. This auto-tuning subsystem improves sensitivity for NMR and NQR detection systems.

Q-Damping Subsystem

The inventions active Q-damping sub-system 10 (FIG. 1) allows the τ time period between pulses in the pulse sequence signal to be reduced. The reduction in the τ time maximizes the signal obtained during each part of the pulse sequence and therefore TID increases allowing for more signal to be acquired per unit time. An example of sensitivity increase afforded by a Q-damping subsystem provided by the instant invention increase the signal-to-noise ratio by 10 which translates into a 100-fold decrease in scan time.

Problems with current receiving RF coil detection receiver capabilities include inadequate receiver characteristics as well as a prolonged ringing signal after a pulse transmit event. The ringing signal has a characteristic decay time Tr. The receiver or antenna is a tuned LC (inductor/capacitor) tank circuit which includes the active coil (RF coil) in close proximity to which a specimen under investigation is placed. The "sensitivity" of the antenna is dependent on a number of factors including the signal-to-noise ratio which is defined by the following equation:

$$\text{Signal-to-Noise Ratio} = \{\text{const.}\} (Q/V)^{1/2} \cdot \omega^{3/2} \quad (1)$$

wherein ω is the precession tuning frequency, V is the confined volume and "Q" is the quality factor of the circuit coil. Thus, the higher the Q, the greater the coil sensitivity. The ringing signal is generated as a result of applying and receiving an RF pulse using a high-Q detection NQR/NMR detection receiver. The magnetic field generated within the RF coil persists after the pulse has finished resulting in a decaying ringing voltage signal within the RF coil. The characteristic decay time for this ringing signal is partially dependent upon Q and is phase coherent with the nuclear induction signal. The ringing signal in some circumstances can also contain other components such as eddy currents, magneto-elastic and other related phenomena. The magnitude of the ringing signal is dependent on the frequency and the Q of the RF coil, the relationship is shown in the following equation:

$$\tau = 2Q/\omega \quad (2)$$

where τ is the ring down time constant, Q is the quality factor of the RF coil and ω is the tuned precessional frequency 2πf. This ringing signal occurs simultaneously with the nuclear induction signal and drowns it, making it undetectable until the ringing signal has decayed to low enough level. A nuclear induction signal can still be obtained provided that the ringing has a shorter characteristic decay time than the detected signal. This does not always happen since the exact nuclear induction signal decay characteristic of the specimen material depends on the molecular environment.

The Q-damping subsystem 10 effectively increases the equivalent series resistance or decreases the equivalent parallel resistance of the RF coil 34 to maximize the SNR and minimize signal acquisition dead time. The subsystem 10 interconnects with the NQR system (FIG. 1) through terminals a, b and c. As an example, during a transmitting pulsing event, given that the input voltage on a typical 50 ohm port to the RF coil reaches around 250 volts and the subject specimen material is a nitrogen-containing compound whose resonant tuned frequency is 900 kHz and time constant of 215 microseconds, a corresponding received signal coming out of the 50 ohm port is around 10 nanovolts. The "ring-down time," which is typically 10–25 ring-down time constants, is about 5.15 milliseconds. The received RF signal cannot be perceived until the ringing decreases to about the signal level where the ringing can be partially canceled. Without additional Q-damping of the RF coil circuit, the minimum pulse spacing must be greater than 5 milliseconds. For improved signal-to-noise ratio, the number of data acquisitions are increased to a limit of $T_{2eff}$ (the time from a given pulse echo of the pulse train in which the corresponding echo amplitude is 1/e of the amplitude of an echo at a time $T_{2eff}$ previous), and the capabilities of the detection system. For a nitrogen containing explosive material using pulse spacing of 6 milliseconds, the $T_{2eff}$ is about 0.25 seconds which allows for 40 data acquisition events in that time. For a pulse spacing of 1.6 milliseconds, $T_{2eff}$ for a nitrogen-containing material is approximately 8.4 seconds which allows for about 5000 acquisition events, that is, over a 10-time improvement in the signal-to-noise ratio. The Q factor in a parallel RLC circuit is inversely proportional to the shunt resistance; in a series RLC circuit, the Q value is directly proportional to the series resistance. If the Q value in the RF coil circuit were reduced for all system operations, it would: i) raise the transmit power required during the pulse on-time provided that the pulse width is greater than τ, the ring-down time constant; and ii) lower the receiver sensitivity by diminishing the effectiveness of the RF coil. This is not a desirable state. Thus, in accordance with this invention, lowering the Q value during certain periods of the RF signal transmit and receive brings about desirable operating condition.

Figure 5A:
FIGS. 5A and 5B are wave-form diagrams of an RF pulse in detection systems exhibiting pulse characteristics with and without Q-damping respectively.
Figure 5B:
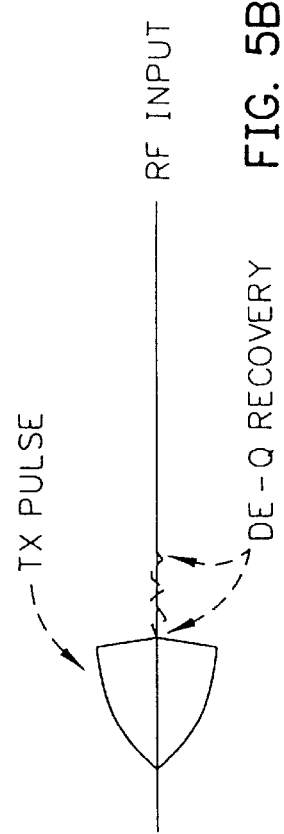
Figure 5C:
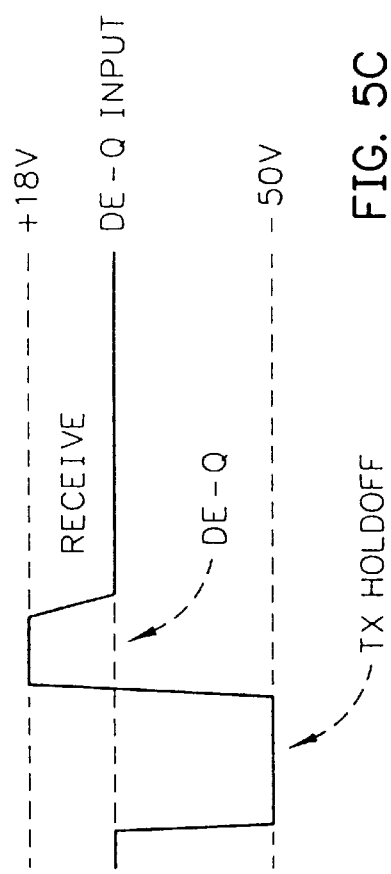
FIG. 5C shows a control timing signal for controlling Q-damping as shown in FIG. 5B.

FIG. 5A shows a non-Q-damped RF signal response with a long τ time period whose ring-down time occurs during a signal acquisition period, and FIG. 5B shows a Q-damped RF signal with a short τ time period. In particular, transmission of the TX pulse as shown in FIG. 5A is without Q-damping. FIG. 5B shows a Q-damped pulse and FIG. 5C shows the associated control signal where the de-Q'ing circuit input signal is driven negative during the input RF pulse event and driven positive immediately thereafter, then driven negative during receive after the RF coil has "rung down" sufficiently. This occurs when the ring-down level is less than the minimum detectable signal at the current operating conditions. If the operating conditions change (i.e. changing the number of averages), then the definition of sufficiently rung down correspondingly changes.

Active Q-damping circuit networks discussed below modify the shunt resistance coupled to the resonant LC transmitter/receiver in the detection receiver. These Q-damping circuits use similar power supply electronics and software control methodology. The switching elements used are typically high voltage power MOSFET's. The common methodology is having the diodes reversed biased during the transmit and receive modes of operation, and forward biased for a short interval after the end of a transmit pulse event. By Q-damping by active damping during an auto-tuning procedure of the NQR/NMR system, auto-tuning greatly reduces variation in Q of the system, thus resulting in an auto-tuning method which is simpler and faster. The auto-tuning can occur as a sample moves into an examination cavity rather than having the sample in the cavity and then tuning the system. This provides greater capacity of baggage handling capability at an airport. These Q-damping circuits have applications to every high to medium Q-based NQR or NMR system including, but not limited to; hold and cabin baggage screening systems; portal screening systems for airline passengers; antipersonnel and antitank mines; unexploded ordinance; detection devices; and commercial process and control applications. Also, Q-damping can be used many different detection coil types, for example: solenoid; single-sided gradiometers, and the like.

Problems that are need to be minimized when designing and constructing the the Q-damping coil and circuit network 10 include: a) RF noise injection caused by inadequate shielding of the subsystem 10; b) injecting more ringing signal when the diodes turn off (which is a problem not recognized by the U.S. Pat. No. 5,546,00 as discussed above); c) diodes turning on during the transmit pulse from excessive coupling or insufficient reverse bias; and d) insuffient coupling of the Q-damping network to the sample coil.

Opto-isolators are used in association with the Q-damping driver circuits to reduce RF noise injection. These driver circuits also use controlled bias turn-off to reduce ringing, use sufficiently high reverse voltage bias turn-on during transmit, and insure sufficient coupling.

Transformer Coupled Circuit Network

Figure 6:
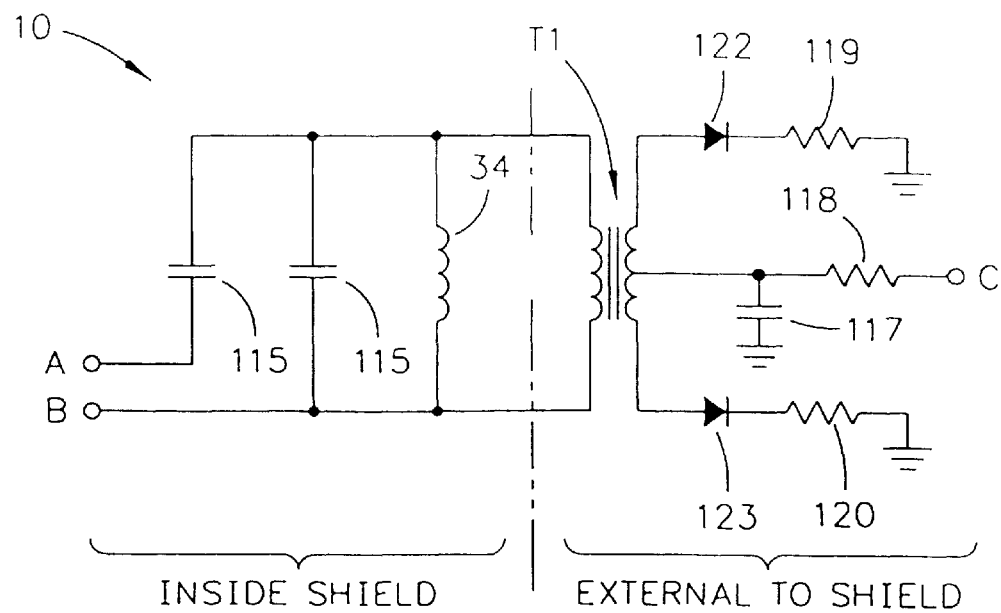
FIG. 6 shows a transformer coupled Q-damping RF circuit of the invention.

FIG. 6 shows a first circuit network which relies on transformer coupling between the RF coil and the shunt resistance using active Q-damping of the RF coil 34 which includes: a) the RF coil 34 with matching auto-tune capacitors 115 which connect to the matching network & Balun 35; and b) the Q-damping section with a ferrite or iron powder cored transformer TI, two RF-type diode switches 122, 123 and two Q-damping resistors 119, 120. The transformer TI is characterized as having a high-Q design, low loss, has a center tap and is in a turns ratio of around 4:1. The shunt capacitor is controlled by controller 21 through resistor 118.

Inductively Coupled Circuit Network

Figure 7:
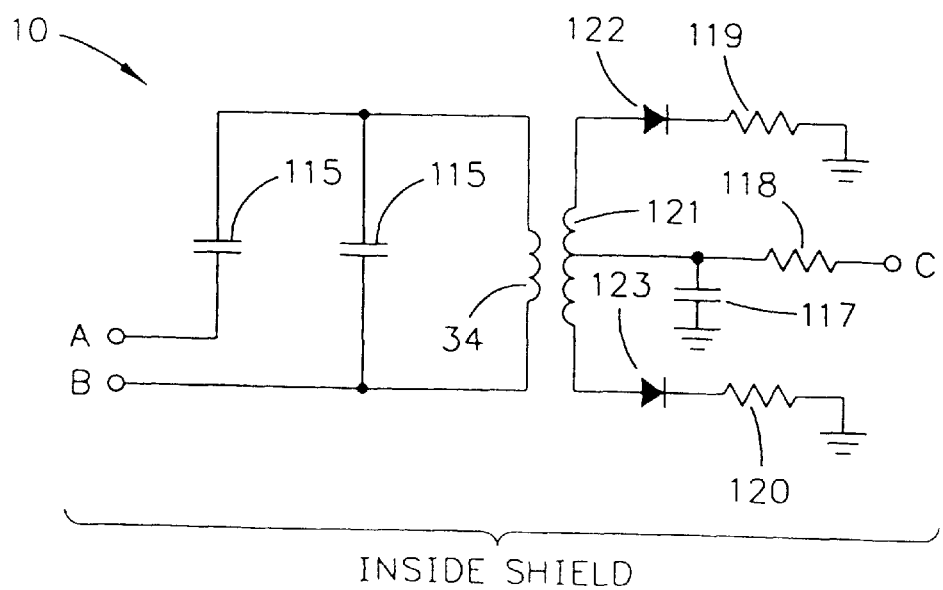
FIG. 7 shows a direct inductively coupled Q-damping circuit of the invention.

FIG. 7 shows the second active Q damping network 10 which is similar to the transformer coupled network design of FIG. 6, but without need of a transformer TI. This network relies on direct inductive coupling between RF coil 34 and shunt resistance 118. The coupling of the RF-type diode switches 122, 123 is via a separate coil 121 placed in close proximity with the RF coil 34. The shunt capacitor is controlled by controller 21 through resistor 118. This network is suited for NMR applications where presence of a ferrite or iron powder core transformer interferes with the homogeneity of an applied static magnetic field. Typical components used high power diodes and carbon based resistors. The voltage ratings of the the diodes are at least twice the peak RF voltage induced in the coil. The resistance value is approximately in a range of to the operational inductive reactance value of the coil in the range of operationg frequency.

Mode of Operation

The mode of operation for both circuits in FIG. 6 and FIG. 7 is the same. A stepped voltage is applied to the diode switch array and timed to optimally reduce the "dead time" which is the total time from the end of the RF pulse to the time when accurate data can be collected, (it includes the sum of all recovery times, ring down time, damp time and delay times). The Q-damping network 10 is controlled by the controller 21 (FIG. 1). Proper operation requires accurate and reproducible control signals for controlling the diodes. The "hold-off" and de-Qing are generated from the pulse programmer 21 that outputs a series of timed pulses to operate the Q-damping network 10.

An exemplary switching timing sequence for the diodes is shown in FIGS. 8A, 8B and 8C. The mode of operation is split into two parts. The first part is referred to as the "hold-off" where a large negative voltage is applied to the two diodes to inhibit conduction during the application of the high voltage RF pulse. This "hold-off" voltage is applied only during the pulse. As soon as the pulse terminates, the diode bias voltage is changed in sign and becomes positive causing the diodes to conduct. The length of Q damping time is set experimentally and depends on the amount of magnetic energy in the RF coil 34 that needs to be conducted away. The Q-damping time is always shorter than the natural ring time for the RF coil 34. After the Q-damping time the positive switching voltage is left to float and eventually reach ground potential. Hard switching to the off state is not desirable since excessive induced ringing occurs and interrupts optimal circuit operation.

Figure 9A:
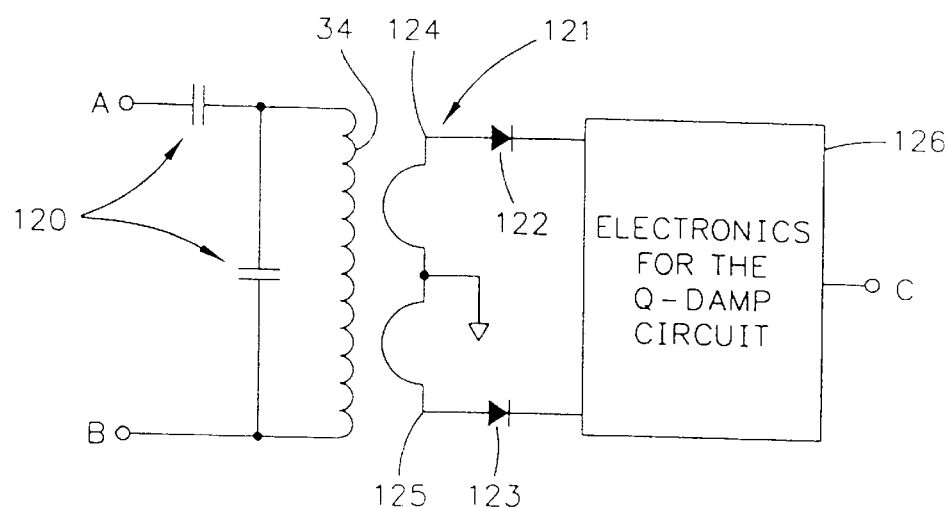
FIGS. 9A, 9B, 9C, 9D and 9E show the design for the Q-damp coil and associated electronic components for the Q-damping subsystems shown in FIGS. 10A–14C.
Figure 9B:
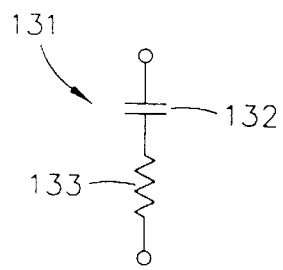
Figure 9C:
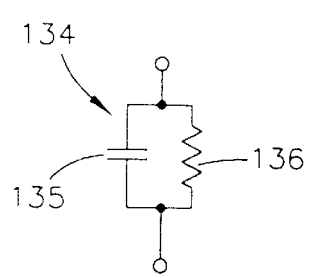
Figure 9D:
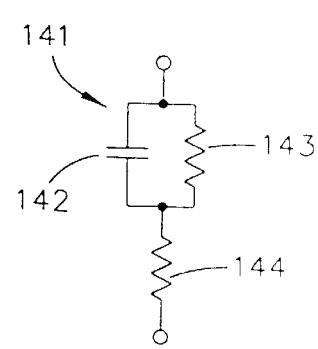

FIG. 9A provides a generic version of a Q-damping circuit coupled to RF coil 34 in a manner similar to the FIG. 7 embodiment with the addition of a network to the Q-damp circuit to permit tuning to a lower Q than would be possible with the Q-damp circuit above. Q-damp coil 121 provides the inductive coupling to RF coil 34 and is center tapped to ground. Diodes 122 and 123 directionally couple respective ends 124 and 125 of the Q-damp coil to the Q-damp circuit electronics 126. The electronics block includes capacitor 117, Q-damping resistors 119 and 120 and output resistor 118 in the output line to terminal C of FIG. 7. FIGS. 9B–9D show example networks which are connected between the Q-damp diodes on the circuit side, that is, between diode 122 and resistor 119 on one side and diode 123 and resistor 120 on the other side. Further details follow hereinbelow.

FIGS. 9A, 9B, 9C, 9D and 9E provide definition to the Q-damping circuit networks that follow which use the following terminology:

The "equivalent series resistance" (ESR) for a diode is a function of the D.C. bias current through the diode, also referred to as the small signal impedance.

"Induced Transients," also known as a "Glitch" is noise injected into the detection system that is caused by switching. Typical sources of induced transients are, but are not limited to; capacitive charge injection, inductive mismatch, radiated noise and conducted noise, and unequal reverse diode recovery.

"AutoTuning" are system adjustments by the system hardware and software to adjust the detection coil back to the NQR frequency of interest after a sample is placed in proximity to the detection coil which consequently causes a frequency shift.

"Tune" are adjustments to system components to minimize dead time that is usually done one time for a specified material being examined for.

"Dead Time" is time from the end of the RF pulse to the time when accurate data is acquired. Dead time includes the sum of all recovery times, ring down time, damp time, delay times, etc.

"Recovery Time" is the time a specific circuit transitions from an active to an inactive state that includes diode, transistor and RC transient recovery times.

"Ring Down Time," is typically 10 to 25 time constants. The ring down time constant is $\tau=Q/(\pi F)$.

"Damp Time" is time spent in a low-Q-state.

"Delay Time" is propagation delays.

The preferred connection of the diodes is the anode to coil side and cathode to circuit side. This type connection allows the use of high-voltage NPN transistors and/or high voltage N-channel type MOSFET's. NPN transistors and N-channel MOSFETs are the preferred types of switching elements since they are readily available, lower priced and offer greater selection than do PNP-transistors and P-channel MOSFETs. The switching diodes are grounded through low valued resistors when switched-on. The representative Q-damping circuit in FIG. 9A shows the resonating and matching capacitors 120 which are the auto-tuned capacitors with the RF coil 34 as shown in FIG. 7. The "Q" damp coil 121 with preferred diode orientation as shown is incorporated with each of the designs shown in FIGS. 10A–10D below. Note that the individual "Network" as labeled refers to either the series sub-network shown in FIG. 9B, a parallel sub-network shown in FIG. 9C, or a combination series/parallel sub-network shown in FIG. 9D whose series element can be either a resistor or capacitor. Series network 131, comprising capacitor 132 and resistor 133 is shown in FIG. 9B. FIG. 9C shows parallel network 134 comprised of capacitor 135 and resistor 136. Combination series/parallel network 141, comprises capacitor 142 and resistors 143 and 144 (FIG. 9D). The drive for the Q-damping circuit which is preferably a filtered, opto-coupled digital source that controls the switching of the diodes by the sequence controller 21 of the system as shown below in specific circuit topologies.

Shunt Capacitor-Resistor Circuit Network

Figure 10A:
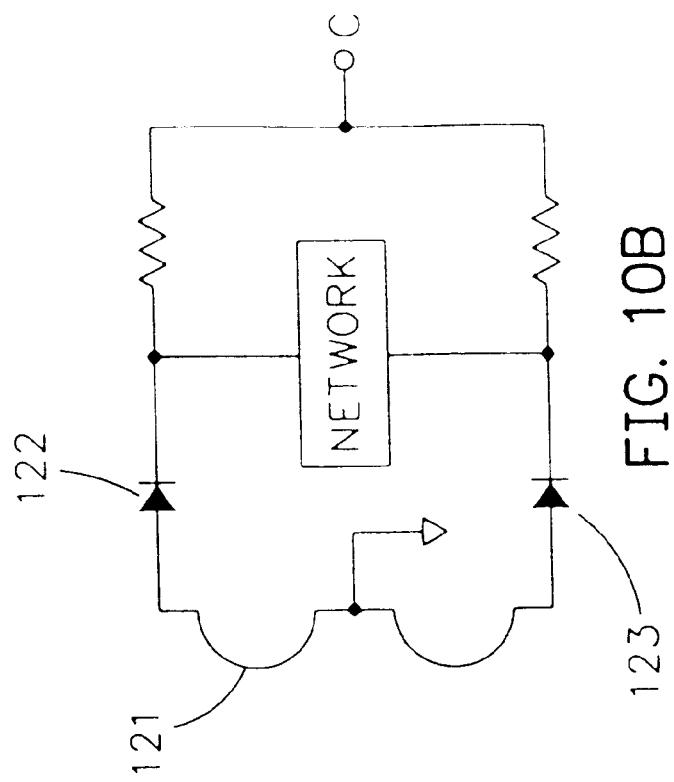
FIGS. 10A and 10B show two versions of a shunt capacitor/resistor damping circuit for use in the Q-damping circuit of the invention.
Figure 10B:
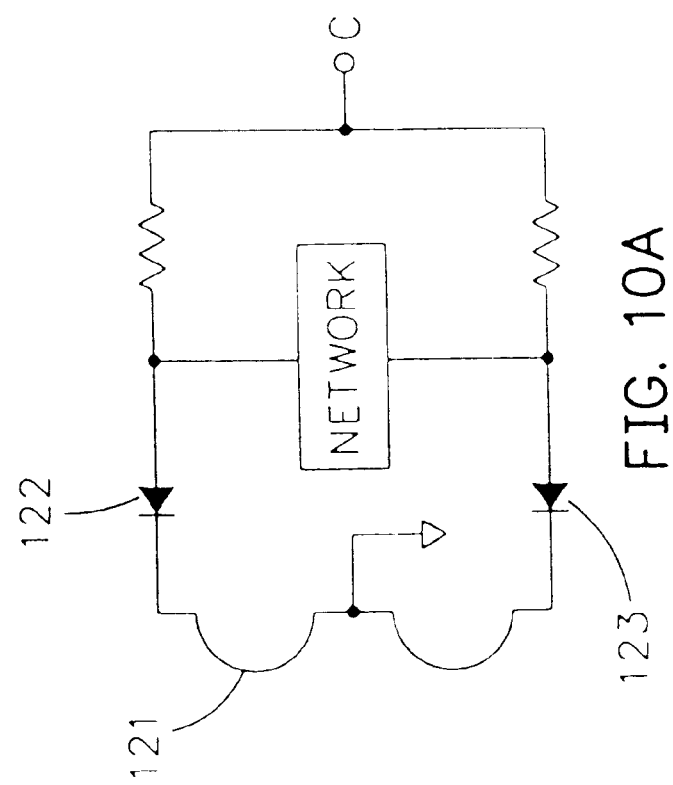

FIGS. 10A and 10B are alternative arrangements of the diodes in the Q-damp circuit with one of networks 131, 134 or 141 connected therein. The capacitor and resistor values used in the "Network" are chosen to tune the Q-damping circuit for the desired damping and phase change. The resistor values can range from around zero ohms to several megohms. The capacitor values can range from the low pico-farads (pf) to several micro-farads ($\mu$f). The total resistance of the loop is a combination of the resistance of the coil wire, the resistor itself and the ESR of the diodes. The addition of this network to the Q-damping circuit allows tuning to a lower Q than would otherwise be possible with the Q-damping circuit standing alone. With a lower Q during the ring down time, there can be less dead time and data acquisition can start sooner, increasing the SNR. This network effectively reduces the "Q" of the NQR detection coil to remove energy therefrom.

Figure 9E:
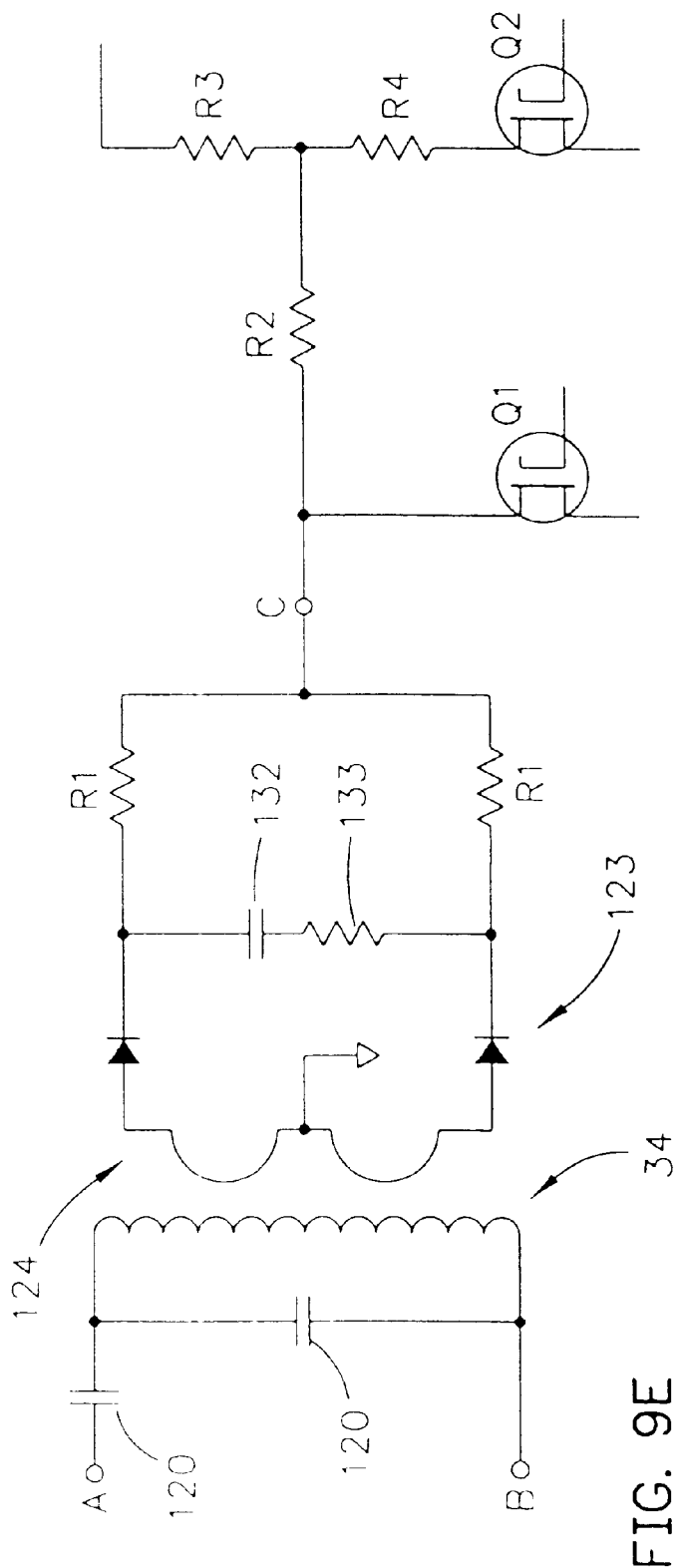

A specific preferred example of this Q-damping circuit network is referred to as a diode recovery time tuning circuit is shown in FIG. 9E. This circuit has the driver circuit connected at the node C. The driver circuit includes a resistor R2, R3 and R4 and two switching devices Q1 and Q2 that are controlled by the sequence controller 21. Resistor R1 is a balancing element. The R2 resistor between the switching "on" transistor Q1 and the and the receive "on" voltage reference biased by the resistors R3 and R4 allows for tuning of the diode recovery time. An advantage of this circuit is that it minimizes transients caused by the diode switching action in the Q-damping circuit by reducing induced transients, thus reducing dead time. With shorter dead time, more data can be acquired for a given time period resulting in greater SNR. The diode recovery time circuit design effectively reduces or obviates the "glitch effect" when turning the Q-damping circuit on and off.

Grounded Shunt Capacitor/Resistor Network

Figure 11A:
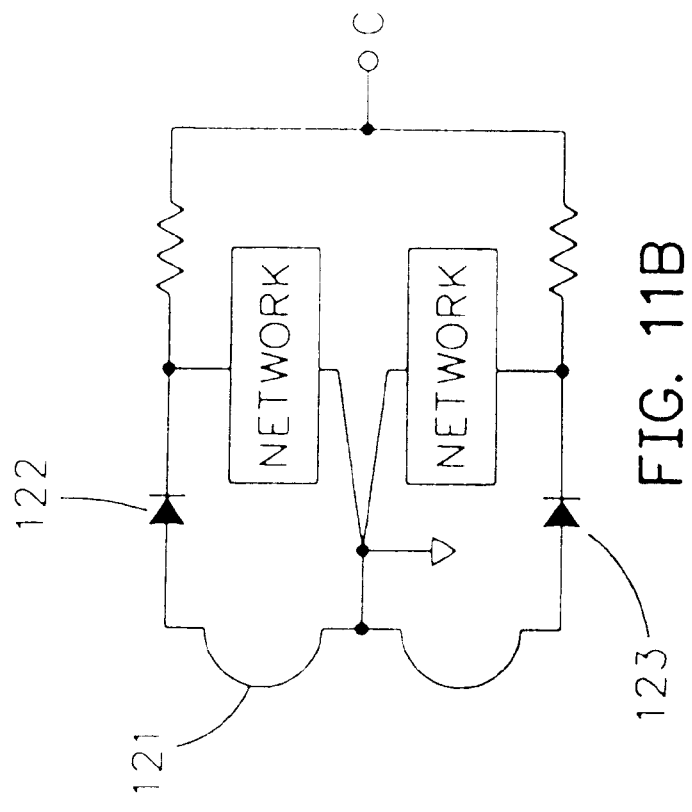
FIGS. 11A and 11B show two grounded shunt capacitor/resistor damping circuit designs, a common mode choke transient suppression damping circuit, a multi-stage Q-damping circuit and a full-wave Q-damping circuit for use in the Q damping circuit of the invention.
Figure 11B:
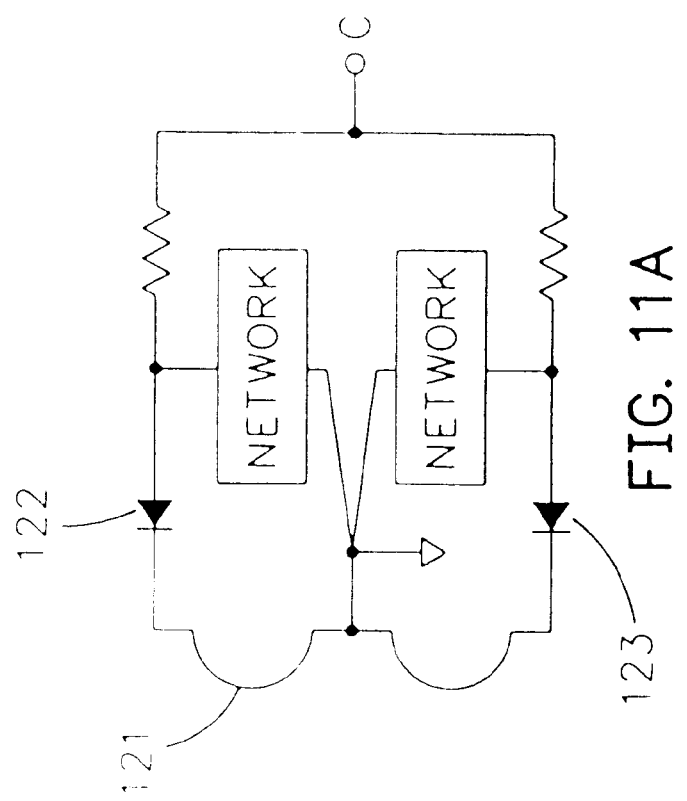

FIGS. 11A and 11B show alternative arrangements of the diodes, as in FIG. 10 in a shunt resistor/capacitor Q-damping circuit design that use any two of the networks shown in FIGS. 9B–9D above. One network is needed for each side and is placed between the Q-damping diode and ground on the circuit side, as previously explained. The resistor and capacitor values can have the same range as in FIGS. 10A–C. The total resistance of the loop is also the combination as described with respect to FIGS. 10A–C. The grounding of the capacitor/resistor network reduces induced transient noise generated when the Q-damping circuit is switched on or off by minimizing the charge injection induced transients due to switching the Q-damp circuit on or off. This network also permits tuning to make the "Q" even lower then otherwise possible using the Q-damping circuitry alone. This network effectively reduces the "Q" of the NQR detection coil to remove energy therefrom.

Common Mode Choke Transient Suppression Network

Figure 12B:
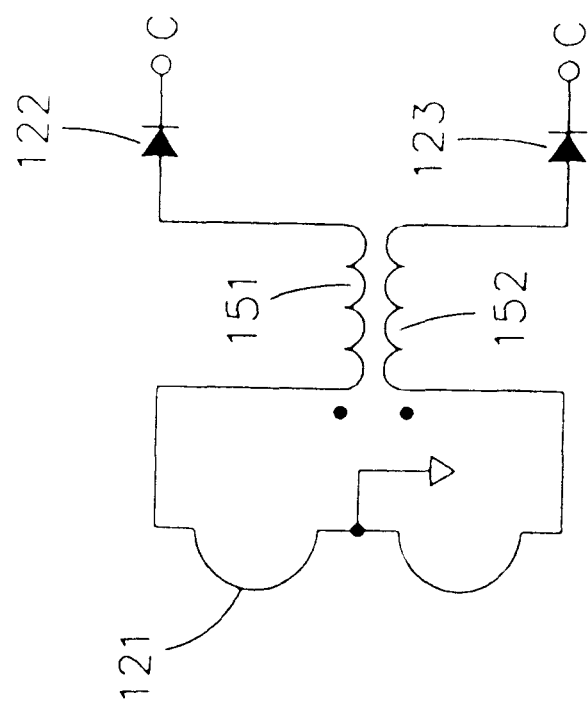
FIGS. 12A and 12B show two versions of a common mode choke transient suppression damping circuit for use in the Q-damping circuit of the invention.
Figure 12A:
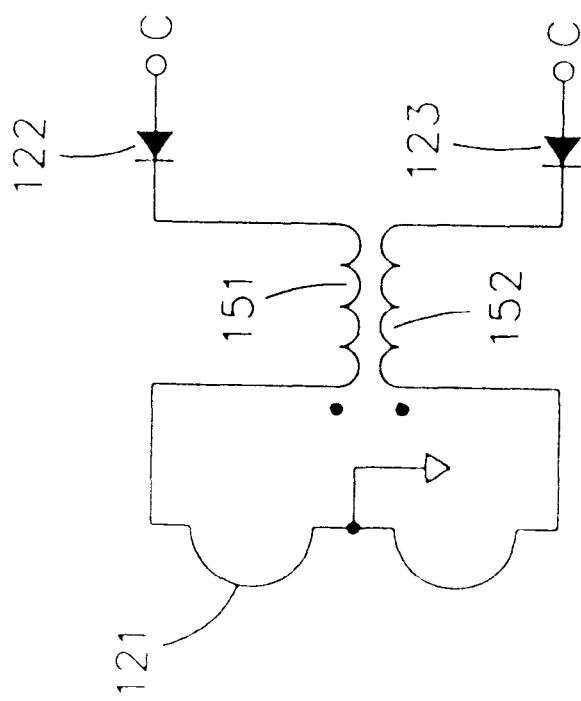

FIGS. 12A and 12B are alternative diode arrangements similar to FIG. 10, showing a common mode choke transient suppression network placed between the Q-damp coil 121 and the diodes 122, 123. The choke comprises coupled coils 151 and 152. This network attenuates common mode "induced transients." This network assists tuning of the Q-damp circuit by making the system less sensitive to a faster switching of the Q-damping circuit. With faster switching, the dead time is reduced. This network design effectively reduces or obviates the "glitch effect" when turning the Q-damping circuit on and off.

Multi-Stage Q-Damp Circuit Network

Figure 13B:
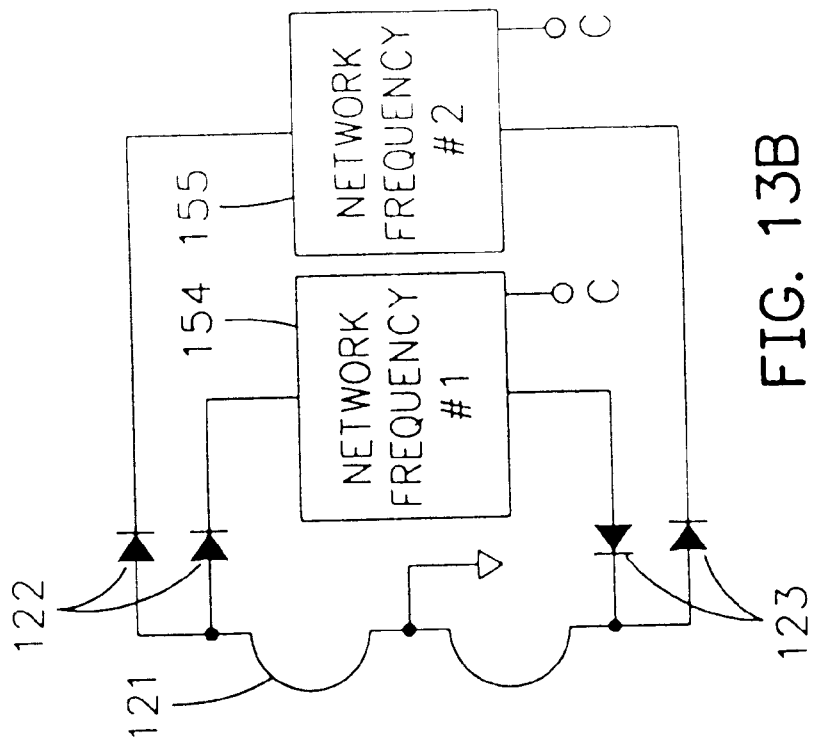
Figure 13A:
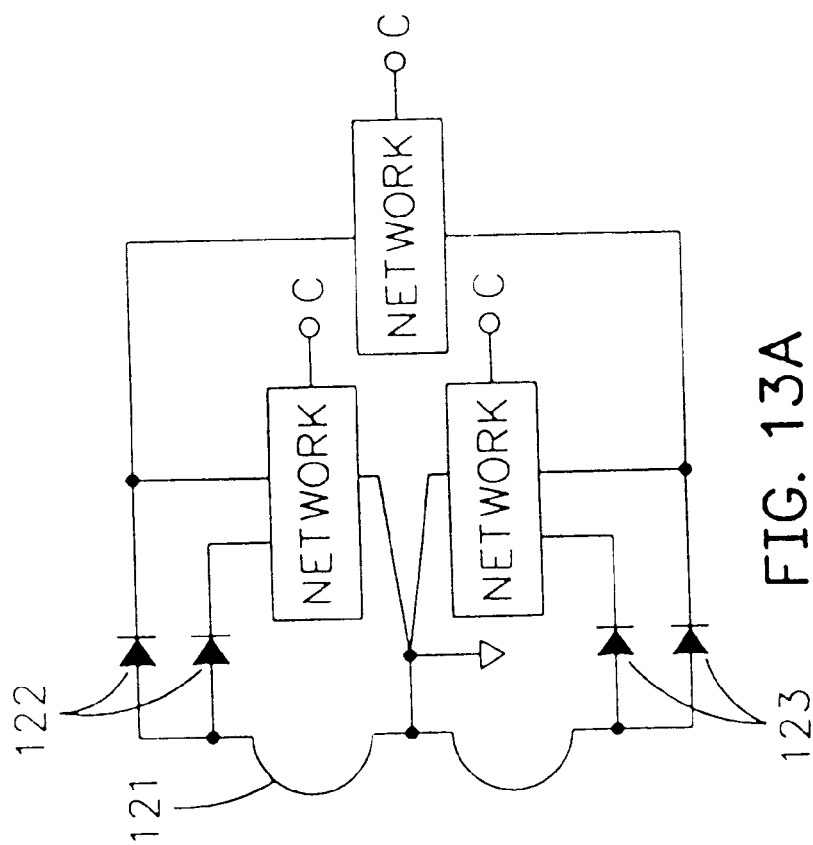

FIGS. 13A and 13B show alternative embodiments of a multi-stage Q-damping circuit made up of two or more Q-damping circuits attached to the same coil. In FIG. 13A the "Network" can be any of those circuits are shown in FIGS. 9B–9D. These stages can be the same or different circuits. When the circuits are the same a lower Q may result, reducing the damp time and improving the SNR. With different circuits, a combination response can be obtained, that is, a low-Q state occurs along with low induced transients during turn off or on. A combination response can also be realized by changing the timing of the on-off cycle of each stage. Multiple stages with individual stage timing is achievable with minimal overall system degradation. Another version is to tune Q-damping for different frequencies, employing Network Frequency circuits 154 and 155. With multi-stage Q-damping circuit networks, the sequence controller 21 can be programmed to select different Q-damping stages for each step in the detection process. For example, a first stage network can enable a reduced "Q" damped state to facilitate a frequency auto-tune sequence, a second network stage can faciltate an optimized Q-damped (tuned) state for nitrogen-containing material NQR detection, and a third network stage can facilitate an optimized Q-damped (tuned) state for other types of nitrogen containing materials using NQR detection and additional stages as required. This network effectively reduces the "Q" of the NQR detection coil to remove energy therefrom.

Phase-Inverted Pulse

Figure 13C:
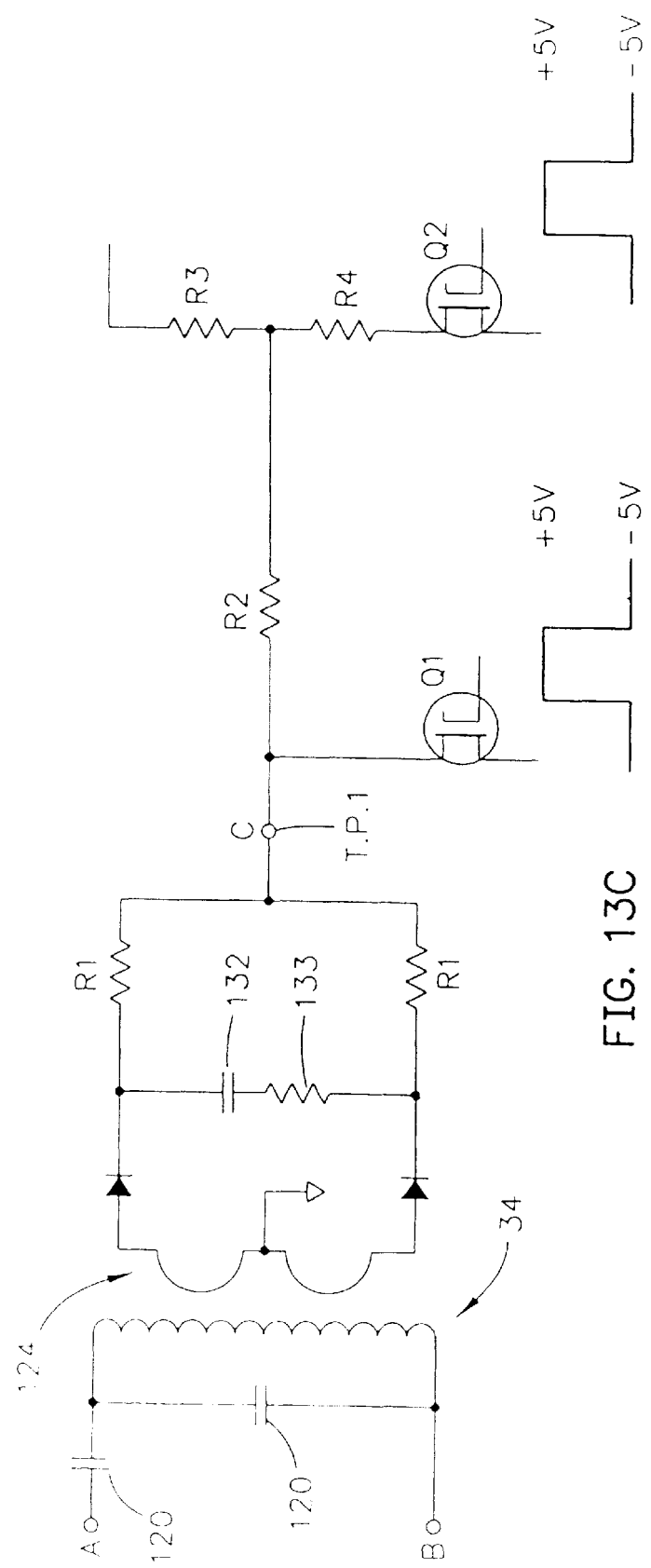

The multi-stage Q-damping circuits can include a phase-inverted pulse as one of the multi-stages. Shaping of the phase-inverted pulse is a variation of using this circuit design. The phase-inverted pulse following a transmit pulse to Q-damp is well known in the art, for example, see the article by Hoult, D. I. entitled "Fast Recovery, High Sensitivity NMR Probe and Preamplifier for Low Frequencies," in *Review of Scientific Instrumentation*, Vol. 50, No. 2, pages 193–200 (1979). The phase-inverted pulse circuit alone has drawbacks since it does not exhibit satisfactory ring-down time. Using another form of Q-damping with the phase inverted pulse damping eliminates most of the phase-glitch, phase stability and timing stability requirements associated with a phase inverted pulse only Q-damping. With a phase inverted pulse damping only system, any input that is slightly out out of phase with ringing in the detection coil will be in a high-Q state and be highly amplified. Including another Q-damping circuit with the phase inverted pulse forces the detection coil to be in a low-Q state, thereby only amplifying glitches slightly. Such problems are minimized when the phase inverted pulse design is included with another Q-damped circuit. When the phase inverted pulse operates simultaneously with other Q-damped circuits further reduced the dead time is acheived. Using phase-inverted pulse greatly reduces the Q-damp circuit complexity and cost, because it is primarily a software change. Moreover, using phase-inverted pulse expends most of the energy stored in the RF coil in the RF power amplifier, eliminating the need for costly high power components in the Q-damp circuit. FIGS. 13C and 13D show the preferred design for this type of network using a phase inverted pulse operating scheme with accompanying timing diagram for operating the Q1 and Q2 switches. The shunt capacitor-resistor sub-network as similarly shown in FIG. 9B is used in the Q-damping circuit shown in FIG. 13C.

Full Wave Q-damp Circuit Network

Figure 14A:
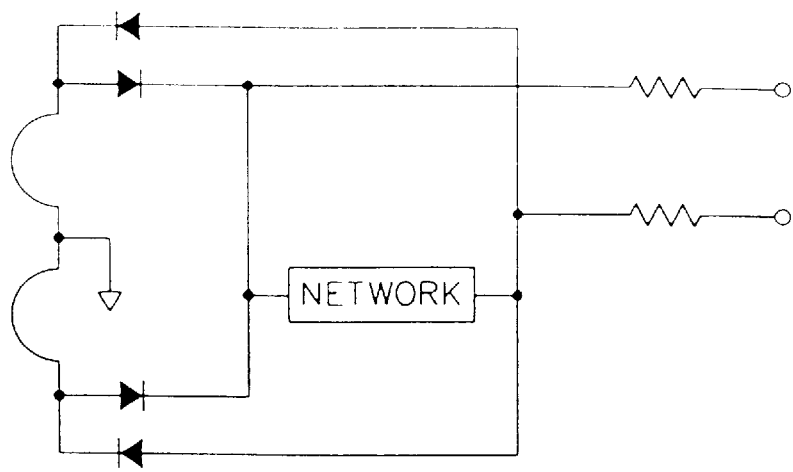
FIGS. 14A, 14B, 14C and 14D show various versions of a full-wave Q-damping circuit for use in the Q-damping circuit of the invention.
Figure 14B:
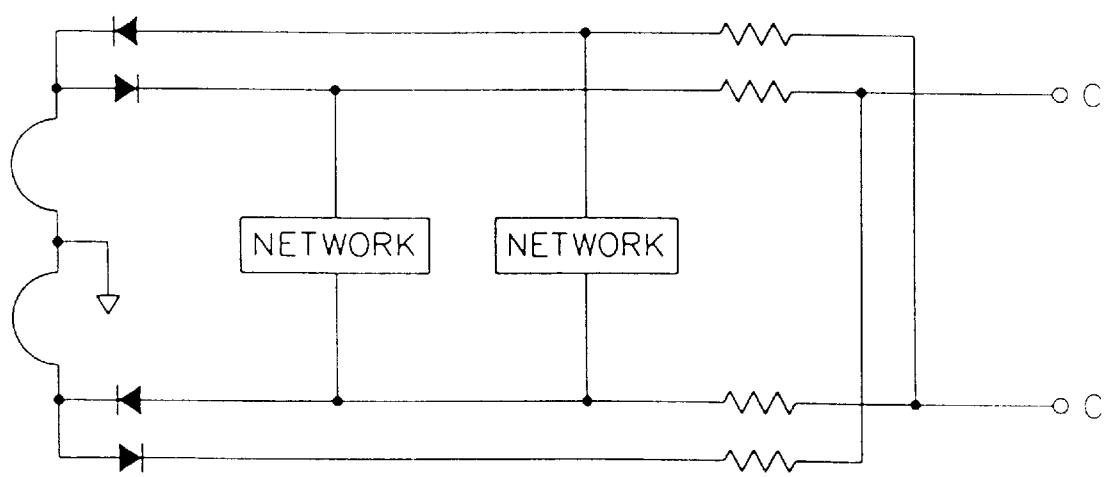

FIGS. 14A and 14B show alternative Q-damp circuits which include four fast recovery diodes in a full wave bridge configuration. The "Network" in each of these configurations may comprise any of the sub-networks shown in FIGS. 9B–D in the FIG. 11 arrangement. The parallel network in FIG. 14A is the preferred circuit. The alternative circuit of FIG. 14B has more components and is more difficult to tune. In each of these full-wave bridge configurations, the diodes are always in a forward conduction mode when Q-damping. Additionally, high RF power can be used without having carrier depletion and reversion to a high-Q state for half-cycle, as happens when using diodes. This network effectively reduces the "Q" of the NQR detection coil to remove energy therefrom with or without use of the phase inverted pulse control scheme. This circuit topology also reduces "Q" to assist in frequency auto-tuning of the NQR system.

Figure 14C:
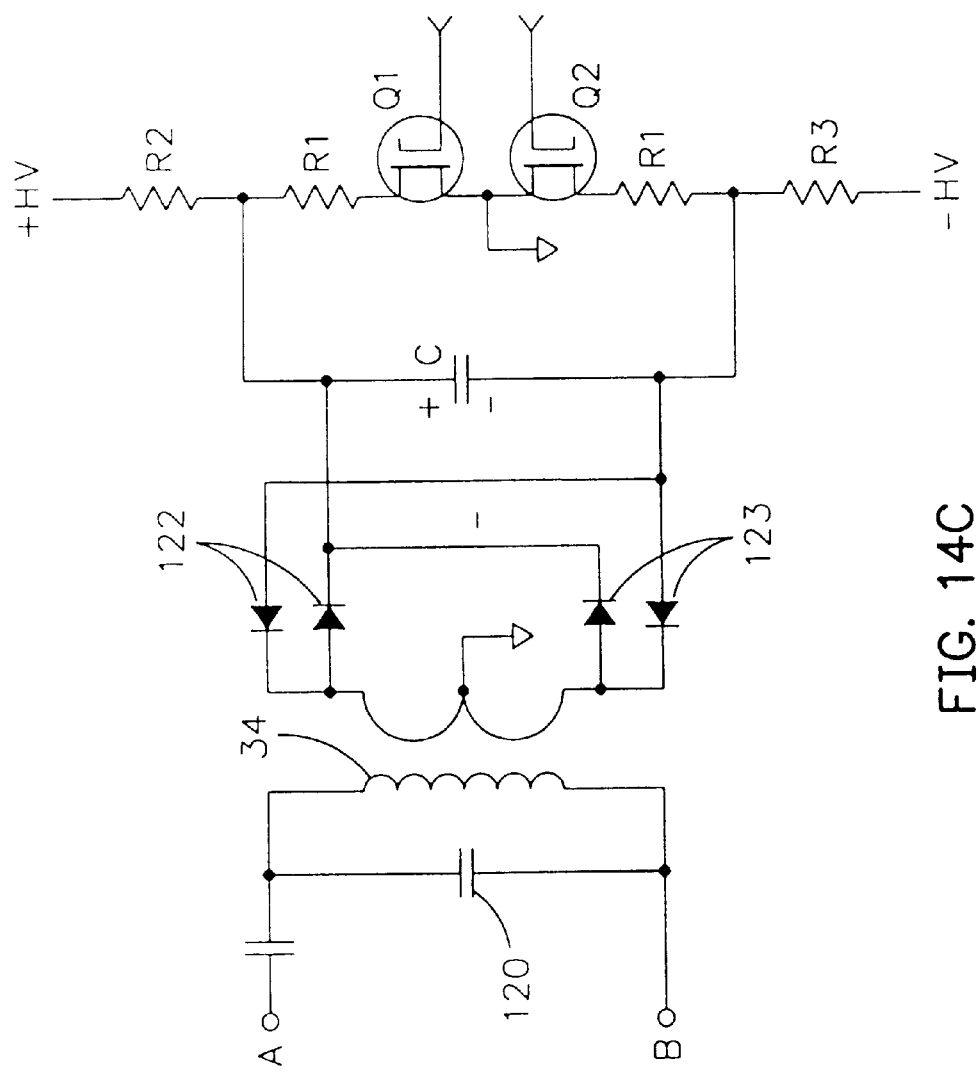
Figure 14D:
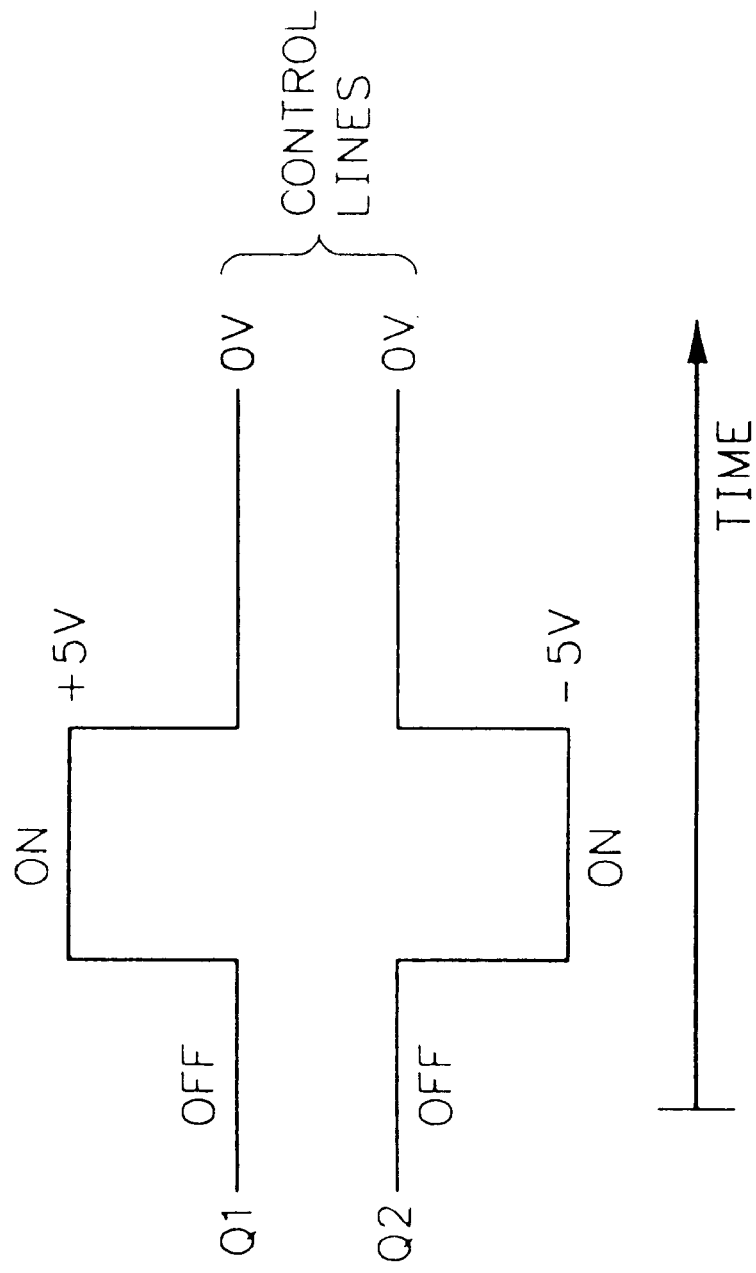

FIG. 14C shows an exemplary example of a full-wave Q-damping circuit comprising an R1 and C subnework in parallel with another RC subnetwork circuits attached to the same Q-damping coil. FIG. 14D shows the logic control signals for switching Q1 and Q2 off and on by the sequence controller 21.

Another variation of the invention involves a Q-switch that supplements the active Q-damping embodiments discussed above allowing the Q of the RF coil to be switched during a transmit pulse. The Q switch device is a separate subsystem to Q-damping subsystem 10 (FIG. 1). The Q switch lowers the Q of the coil during transmit to decrease the pulse ringup time and aid the Q-damping circuit sub-system 10 in reducing the ringdown time. Decreasing the ringup time has two advantages. First, it increases the irradiation bandwidth of a pulse and secondly, it allows the pulse to be shorter by increasing dB/dt. Increased irradiation bandwidth reduces detection problems caused by unknown sample temperature and shorter RF pulses increase QR signal amplitude as the pulse sequence that generates the QR signal is more efficient. The Q switch is based upon a overcoupling network with the addition that transmitter impedance matching is maintained.

The invention has been described above. It is likely that modifications and improvements will occur to those skilled in this technical field which are within the scope of the appended claims.

What is claimed is:

1. A quality factor damping (Q-damping) subsystem for use in a system for detecting substances in a specimen placed in a cavity of the system by means of nuclear quadrupole resonance (NQR) or nuclear magnetic resonance (NMR), the subsystem comprising:

a sequence controller having means for providing timing and programming pulses to the system;

a variable frequency RF source to provide pulsed RF excitation at predetermined frequencies generally corresponding to resonant frequencies of the specimen;

an RF coil shaped and configured to receive the specimen, the RF signal from the RF source being applied to the specimen through the RF coil, the RF coil also functioning as a pickup coil of NQR/NMR signals from the specimen and providing an output signal; and means for Q-damping the RF coil, which includes an isolated Q-damping coil that is controlled by the sequence controller, the sequence controller further including means for detecting a short spin-spin relaxation time ($T_2$) of the specimen compared to the unmodified receiver dead-time, thereby maximizing RF coil sensitivity and minimizing dead time of the output signal for increasing the signal sampling averaging provided by the short-spin relaxation time.

2. The subsystem recited in claim 1, wherein the means for Q-damping the RF coil comprises a transformer coupled circuit network.

3. The sub-system recited in claim 1, wherein the means for Q-damping the RF coil comprises an inductively coupled circuit network.

4. The sub-system recited in claim 1, wherein the means for Q-damping the RF coil comprises a shunt capacitor-resistor circuit network.

5. The sub-system recited in claim 4, wherein the shunt capacitor-resistor circuit network includes a subnetwork selected from the group consisting of a) a series connected resistor and capacitor, b) a parallel connected resistor and capacitor, and c) a series-parallel combination consisting of resistor and capacitor components.

6. The sub-system recited in claim 1, wherein the means for Q-damping the RF coil comprises a grounded shunt capacitor-resistor circuit network.

7. The sub-system recited in claim 6, wherein the grounded shunt capacitor-resistor circuit network includes two subnetworks, each subnetwork is selected from the group consisting of a) a series connected resistor and capacitor, b) a parallel connected resistor and capacitor, and c) a series-parallel combination consisting of resistor and capacitor components.

8. The sub-system recited in claim 1, wherein the means for Q-damping the RF coil comprises a common mode choke transient suppression circuit network.

9. The sub-system recited in claim 1, wherein the means for Q-damping the RF coil comprises a multi-stage Q-damping circuit network.

10. The sub-system recited in claim 9, wherein the multi-stage Q-damping circuit network includes at least two subnetworks, each subnetwork is selected from the group consisting of a) a series connected resistor and capacitor, b)

a parallel connected resistor and capacitor; c) a series-parallel combination consisting of resistor and capacitor components; and d) phase-inverted pulse.

11. The sub-system recited in claim 9, wherein the multi-stage Q-damping circuit network includes two subnetworks having means for tuning at different frequencies.

12. The sub-system recited in claim 1, wherein the means for Q-damping the RF coil comprises a full-wave Q-damping circuit network.

13. The sub-system recited in claim 12, wherein the full-wave Q-damping circuit network includes at least one subnetwork selected from the group consisting of a) a series connected resistor and capacitor, b) a parallel connected resistor and capacitor, and c) a series-parallel combination consisting of resistor and capacitor components.

14. The sub-system recited in claim 1, and further comprising means for auto-tuning the system at multiple tuned frequencies for detecting different substances in the specimen.

15. The sub-system recited in claim 11, wherein the multi-stage Q-damping circuit network includes a phase-inverted pulse circuit as one of the networks.

16. The sub-system recited in claim 4, wherein the sequence controller generates control signals to a diode recovery time circuit, which in turn controls switching activity of the means for Q-damping the RF coil.

17. The sub-system recited in claim 6, wherein the sequence controller generates control signals to a diode recovery time circuit, which in turn controls switching activity of the means for Q-damping the RF coil.

18. The sub-system recited in claim 8, wherein the sequence controller generates control signals to a diode recovery time circuit, which in turn controls switching activity of the means for Q-damping the RF coil.

19. The sub-system recited in claim 9, wherein the sequence controller generates control signals to a diode recovery time circuit, which in turn controls switching activity of the means for Q-damping the RF coil.

20. The sub-system recited in claim 12, wherein the sequence controller generates control signals to a diode recovery time circuit, which in turn controls switching activity of the means for Q-damping the RF coil.

21. The sub-system recited in claim 15, wherein the sequence controller generates control signals to a diode recovery time circuit, which in turn controls switching activity of the means for Q-damping the RF coil.

22. The sub-system recited in claim 1, wherein the sequence controller generates control signals to a diode recovery time circuit, which in turn controls switching activity of the means for Q-damping the RF coil, the diode recovery circuit has two switching devices wherein the switching devices each connect to outputs from a y-connected resistor device.

23. The sub-system recited in claim 1, wherein a lower dead time leads to increased effective characteristic decay time ($T_{2eff}$), which increases the number of signal samples that can be averaged.

24. A method for quality-factor (Q)-damping (Q-damping) an RF coil in a system for detecting target substances in a specimen by means of nuclear quadrupole resonance (NQR) or nuclear magnetic resonance (NMR) for improving the signal-to-noise ratio of the system and minimizing dead-time of a received RF coil signal, the method comprising the steps of:

inserting the specimen within a cavity formed in the RF coil;

providing RF pulses of predetermined frequencies to the RF coil for predetermined time; and selectively changing the quality factor "Q" of a circuit containing the RF coil to Q-damp the RF coil wherein changing of the Q-factor occurs after each RF pulse is generated and removed as soon as the ring down of a received pulse has decayed below a predetermined level wherein a short spin-spin relaxation time ($T_2$) of a received signal from the specimen occurs compared to the receiver dead-time thereby increasing the sampling signal to be averaged.

25. The method recited in claim 24, wherein the system includes a controller that provides an algorithm for Q-damping of the RF coil, the Q-damping state being accomplished through a plurality of active switching components to which signals are applied from the controller, the switching components form part of a means for Q-damping the RF coil.

26. The method recited in claim 25, wherein the algorithm includes steps for controlling the means for Q-damping the RF coil comprising a multi-stage Q-damping circuit network that incorporates a phase inverted pulse design.

27. The method recited in claim 25, wherein the algorithm includes steps for controlling the means for Q-damping the RF coil comprising a multi-stage Q-damping circuit network which includes two subnetworks having means for tuning at different Q-damping frequencies.

28. The method recited in claim 25, wherein the algorithm includes steps for controlling the means for Q-damping the RF coil further comprising a Q-switch that supplements the means for Q-damping the RF coil, wherein the algorithm includes steps for allowing the Q of the RF coil to be switched during a transmit pulse event, whereby the Q-switch lowers the Q of the RF coil during transmit to decrease pulse ring up time and reduce ring down time of the means for Q-damping.

* * * * *